US008148498B2

(12) United States Patent
Chedid et al.

(10) Patent No.: US 8,148,498 B2
(45) Date of Patent: Apr. 3, 2012

(54) DKK-1 ANTIBODIES

(75) Inventors: Marcio Chedid, Fishers, IN (US); Ryan James Darling, Fortville, IN (US); Rachelle Jeanette Galvin, Fishers, IN (US); Barbara Anne Swanson, Encinitas, CA (US)

(73) Assignee: Eli Lilly and Company, Indianapolis, IN (US)

( * ) Notice: Subject to any disclaimer, the term of this patent is extended or adjusted under 35 U.S.C. 154(b) by 87 days.

(21) Appl. No.: 12/754,637

(22) Filed: Apr. 6, 2010

(65) Prior Publication Data

US 2010/0260754 A1 Oct. 14, 2010

Related U.S. Application Data

(60) Provisional application No. 61/168,411, filed on Apr. 10, 2009.

(51) Int. Cl.
*C12P 21/08* (2006.01)
(52) U.S. Cl. .................................. 530/387.3; 424/133.1
(58) Field of Classification Search ............... 530/387.3; 424/133.1
See application file for complete search history.

(56) References Cited

U.S. PATENT DOCUMENTS

| 7,138,508 | B2 | 11/2006 | Niehrs et al. | |
|---|---|---|---|---|
| 7,371,736 | B2 | 5/2008 | Shaughnessy et al. | |
| 7,446,181 | B2 | 11/2008 | McCarthy | |
| 2004/0009523 | A1 | 1/2004 | Shaughnessy et al. | |
| 2005/0084494 | A1 | 4/2005 | Prockop et al. | |
| 2006/0019895 | A1* | 1/2006 | Shaughnessy .................. | 514/12 |
| 2007/0128187 | A1 | 6/2007 | Allen et al. | |

FOREIGN PATENT DOCUMENTS

| EP | 0975755 B1 | 2/2007 |
|---|---|---|
| WO | 9846755 A1 | 10/1998 |
| WO | 9922000 A1 | 5/1999 |
| WO | 9946281 A2 | 9/1999 |
| WO | 0157190 A2 | 8/2001 |
| WO | 02083921 A2 | 10/2002 |
| WO | 02092015 A2 | 11/2002 |
| WO | 03053215 A2 | 7/2003 |
| WO | 2005028678 A2 | 3/2005 |
| WO | 2006015373 A2 | 2/2006 |
| WO | 2007084344 A2 | 7/2007 |

OTHER PUBLICATIONS

Glinka, et al., "Dickkopf-1 is a member of a new family of secreted proteins and functions in head induction—Antibodies were raised against two synthetic peptides of dkk-1", Nature, 1998, 357-362, vol. 391(22).

Tate, et al., "Human Dickkopf as well as DAN Family Members, Cerberus and Gremlin, are Preferentially Expressed in Epithelial Malignant Cell Lines", J. Biochem Mol Biol & Biophys, 1999, 239-242, vol. 3.

Tian, et al., "The Role of the Wnt-Signaling Antagonist DKK1 in the Development of Osteolytic Lesions in Multiple Myeloma—An antibody from a goat that had been immunized against the entire human DKK1 protein", N Engl J Med, 2483-2494, vol. 349.

Forget, et al., The Wnt pathway regulator DKK1 is preferentially expressed in hormone-resistant breat tumours and in some common cancer types—Analysis of DKK1 expression in human cancer specimens revealed DKK1 expression in breast (21 out of 73), lung (11 outo f 23) and kidney cancers (six out of 20), Br J Cancer, 646-653, vol. 96(4).

Yaccoby, et al., "Antibody-based inhibition of DKK1 suppresses tumor-induced bone resorption and multiple myeloma growth in vivo—DKK1 is a key player in MM bone disease; Dkk1-neutralizing antibody holds promise as a potential new treatment of various disorders related to low bone mass and perhaps osteoporosis", Blood; 2106-2111, vol. 109(5).

Krupnick, et al., "Functional and structural diversity of the human Dickkopf gene family", Gene, 301-313, vol. 238(2).

Sezer, et al., "Myeloma bone disease", Hematology, 2005 19-24, vol. 10 Suppl 1.

Hall, et al., "The role of Wnts in bone metastases", Cancer Metastasis Review, 551-558, vol. 25.

Gregory, "Advances in myeloma therapy:breaking the cycle", Blood, 1798, vol. 109(5).

Ettenberg, et al., "BHQ880, a novel anti-DKK1 neutralizing antibody, inhibits tumor-induced osteolytic bone disease", Proceedings of the Annual Meeting of the American Association for Cancer Research, 2008, p. 947, vol. 49.

Heath, et al., Inhibiting Dickkopf-1 (Dkk1) removes suppression of bone formation and prevents the development of osteolytic bone disease in multiple myeloma, Journal of Bone and Mineral Research, American Society for Bone and Mineral Research, 2009, pp. 425-436, vol. 24 (3).

Hall, Christopher, et al., "Dickkopf-1 expression increases early in prostate cancer development and decreases during progression from primary tumor to metastasis", Prostate, 2008, pp. 1396-1404, vol. 68(13).

Terpos, E., "Antibodies to dickkopf-1 protein", Expert Opinion on Therapeutic Patents, Informa Healthcare, 2006, pp. 1453-1458, vol. 16(10).

Diarra, Danielle, et al., "Dickkopf-1 is a master regulator of joint remodeling", Nature Medicine, 2007, pp. 156-163, vol. 13(2).

* cited by examiner

*Primary Examiner* — Misook Yu
*Assistant Examiner* — Brad Duffy
(74) *Attorney, Agent, or Firm* — Alejandro Martinez

(57) ABSTRACT

The invention provides human engineered antibodies, antigen-binding fragments thereof, that bind to, and inhibit the activity of, human DKK-1, and which are effective in treating diseases in which pathogenesis is mediated by DKK-1.

14 Claims, No Drawings

DKK-1 ANTIBODIES

The present invention relates to human engineered antibodies against DKK-1 and their use in treating diseases in which pathogenesis is mediated by DKK-1.

Dickkopf-1 (Dkk-1) is a member of the dickkopf family of proteins that have been shown to be negative regulators of the canonical Wnt-signaling pathway. The pathway plays a central role in bone development and formation. Dkk-1 inhibits Wnt signaling through its interaction with the Wnt co-receptor LRP5 or LRP6 and the kremen proteins. Dkk-1 prevents members of the Wnt pathway from interacting with either LRP5 or LRP6, thus preventing Wnt-mediated signal transduction. DKK1 has also been shown to be involved in bone metastasizing cancers, including multiple myeloma, breast carcinoma, renal carcinoma and non-small cell lung cancer.

Antibodies that bind Dkk-1 have been described (for example, see WO2006015373), however, there is still a need for therapeutic human engineered DKK-1 antibodies that will inhibit the interaction of Dkk-1 with LRP5 and LRP6. In addition, in view of the involvement of Dkk-1 in the regulation of bone formation, there is a need for therapeutic human engineered anti-Dkk-1 antibodies for use in bone healing. In addition, given the involvement of Dkk-1 in cancers, there is a need for human engineered anti-Dkk-1 antibodies for treating cancers, including multiple myeloma, breast and non-small cell lung cancers.

The antibodies of the present invention are therapeutically useful DKK-1 antagonists possessing a number of desirable properties. The present human engineered antibodies exhibit high affinity (Kd) to human DKK-1, cynomolgus DKK-1, rat DKK-1, mouse DKK-1, and rabbit DKK-1. Antibodies of the present invention block DKK-1-mediated inhibition of alkaline phosphatase, a marker of osteoblast activity. Furthermore, antibodies of the present invention exhibit an increase in bone mass density at both anterior and posterior cortices in a cortical defect in vivo model and demonstrate significant growth inhibition of non-small cell lung xenografts in vivo.

The present invention provides a human engineered DKK-1 antibody or antigen-binding fragment thereof that has a Kd at 37° C. of less than $5.0 \times 10^{-11}$M for human DKK-1 (SEQ ID NO: 29), cynomolgus DKK-1 (SEQ ID NO: 30), rat Dkk-1 (SEQ ID NO: 31), mouse DKK-1 (SEQ ID NO: 33), and rabbit DKK-1 (SEQ ID NO: 32).

The present invention provides a human engineered DKK-1 antibody or a binding fragment thereof wherein LCDR1 has the amino sequence of SEQ ID NO:5, LCDR2 has the amino sequence of SEQ ID NO:47, LCDR3 has the amino sequence of SEQ ID NO:49, HCDR1 has the amino sequence of SEQ ID NO:1, HCDR2 has the amino sequence of SEQ ID NO:2, and HCDR3 has the amino sequence of SEQ ID NO:44.

The present invention also provides a pharmaceutical composition comprising the human engineered DKK-1 antibody or antigen-binding fragment thereof of the present invention and a pharmaceutically acceptable carrier, diluent, or excipient.

The present invention provides a method of healing bone comprising administering a human engineered DKK-1 antibody or antigen binding fragment thereof of the present invention. The present invention also provides a method of treating cancer comprising administering a human engineered DKK-1 antibody or antigen binding fragment thereof of the present invention, wherein the cancer is selected from the group consisting of multiple myeloma, breast cancer and non-small cell lung cancer.

The present invention provides a human engineered DKK-1 antibody or antigen-binding fragment thereof as described herein, wherein the antibody has a Kd of less than $1.5 \times 10^{-11}$M for human DKK-1 (SEQ ID NO: 29). More preferably, the present invention provides human engineered DKK-1 antibody or antigen-binding fragment thereof, wherein the antibody has a Kd of less than $1.0 \times 10^{-11}$M for human DKK-1 (SEQ ID NO: 29). Further preferred, the present invention provides human engineered DKK-1 antibody or antigen-binding fragment thereof, wherein the antibody has a Kd of less than $5.0 \times 10^{-12}$M for human DKK-1 (SEQ ID NO: 29). More preferably, the present invention provides human engineered DKK-1 antibody or antigen-binding fragment thereof, wherein the antibody has a Kd between $0.5 \times 10^{-12}$M and $1.5 \times 10^{-11}$M for human DKK-1 (SEQ ID NO: 29). Further preferred, the present invention provides human engineered DKK-1 antibody or antigen-binding fragment thereof, wherein the antibody has a Kd between $1.0 \times 10^{-12}$M and $1.0 \times 10^{-11}$M for human DKK-1 (SEQ ID NO: 29). The Kd values are established by a binding equilibrium at 37° C. as described in Example 2.

The present invention also provides a human engineered DKK-1 antibody or antigen-binding fragment thereof as described herein, wherein the antibody has a Kd of less than $5.0 \times 10^{-11}$M for human DKK-1 (SEQ ID NO: 29), cynomolgus DKK-1 (SEQ ID NO: 30), rat Dkk-1 (SEQ ID NO: 31), mouse DKK-1 (SEQ ID NO: 33), and rabbit DKK-1 (SEQ ID NO: 32). More preferably, the present invention provides human engineered DKK-1 antibody or antigen-binding fragment thereof, wherein the antibody has a Kd of less than $3.0 \times 10^{-11}$M for human DKK-1 (SEQ ID NO: 29), cynomolgus DKK-1 (SEQ ID NO: 30), rat Dkk-1 (SEQ ID NO: 31), mouse DKK-1 (SEQ ID NO: 33), and rabbit DKK-1 (SEQ ID NO: 32). Further preferred, the present invention provides human engineered DKK-1 antibody or antigen-binding fragment thereof, wherein the antibody has a Kd of less than $2.0 \times 10^{-11}$M for human DKK-1 (SEQ ID NO: 29), rat Dkk-1 (SEQ ID NO: 31), and mouse DKK-1 (SEQ ID NO: 33). More preferably, the present invention provides human engineered DKK-1 antibody or antigen-binding fragment thereof, wherein the antibody has a Kd between $1.0 \times 10^{-11}$M and $5.0 \times 10^{-11}$M for human DKK-1 (SEQ ID NO: 29), cynomolgus DKK-1 (SEQ ID NO: 30), rat Dkk-1 (SEQ ID NO: 31), mouse DKK-1 (SEQ ID NO: 33), and rabbit DKK-1 (SEQ ID NO: 32). Further preferred, the present invention provides human engineered DKK-1 antibody or antigen-binding fragment thereof, wherein the antibody has a Kd between $1.5 \times 10^{-11}$M and $3.0 \times 10^{-11}$M for human DKK-1 (SEQ ID NO: 29), rat Dkk-1 (SEQ ID NO: 31), and mouse DKK-1 (SEQ ID NO: 33). The Kd values are established by a binding equilibrium at 37° C. as described in Example 2.

More preferably, the present invention provides a human engineered DKK-1 antibody or antigen-binding fragment thereof comprising a LCVR comprising the amino acid sequence of SEQ ID NO:14 and a HCVR comprising the amino acid sequence of SEQ ID NO:12 and wherein the human engineered DKK-1 antibody or antigen-binding fragment thereof has a Kd of less than $3.0 \times 10^{-11}$M for human DKK-1 (SEQ ID NO: 29), cynomolgus DKK-1 (SEQ ID NO: 30), rat Dkk-1 (SEQ ID NO: 31), mouse DKK-1 (SEQ ID NO: 33), and rabbit DKK-1 (SEQ ID NO: 32). Further preferred, the present invention provides a human engineered DKK-1 antibody or antigen-binding fragment thereof comprising a LCVR comprising the amino acid sequence of SEQ ID NO:14 and a HCVR comprising the amino acid sequence of SEQ ID NO:12 and wherein the human engineered DKK-1 antibody or antigen-binding fragment thereof has a Kd of less than $2.5×10^{−11}$M for human DKK-1 (SEQ ID NO: 29), cynomolgus DKK-1 (SEQ ID NO: 30), rat Dkk-1 (SEQ ID NO: 31), mouse DKK-1 (SEQ ID NO: 33), and rabbit DKK-1 (SEQ ID NO: 32). More preferably, the present invention provides a human engineered DKK-1 antibody or antigen-binding fragment thereof comprising a LCVR comprising the amino acid sequence of SEQ ID NO:14 and a HCVR comprising the amino acid sequence of SEQ ID NO:12 and wherein the human engineered DKK-1 antibody or antigen-binding fragment thereof has a Kd of less than $2.0×10^{−11}$M for human DKK-1 (SEQ ID NO: 29), cynomolgus DKK-1 (SEQ ID NO: 30), rat Dkk-1 (SEQ ID NO: 31), mouse DKK-1 (SEQ ID NO: 33), and rabbit DKK-1 (SEQ ID NO: 32). Further preferred, the present invention provides a human engineered DKK-1 antibody or antigen-binding fragment thereof comprising a LCVR comprising the amino acid sequence of SEQ ID NO:14 and a HCVR comprising the amino acid sequence of SEQ ID NO:12 and wherein the human engineered DKK-1 antibody or antigen-binding fragment thereof has a Kd between $0.5×10^{−12}$M and $3.0×10^{−11}$M for human DKK-1 (SEQ ID NO: 29), cynomolgus DKK-1 (SEQ ID NO: 30), rat Dkk-1 (SEQ ID NO: 31), mouse DKK-1 (SEQ ID NO: 33), and rabbit DKK-1 (SEQ ID NO: 32). More preferably, the present invention provides a human engineered DKK-1 antibody or antigen-binding fragment thereof comprising a LCVR comprising the amino acid sequence of SEQ ID NO:14 and a HCVR comprising the amino acid sequence of SEQ ID NO:12 and wherein the human engineered DKK-1 antibody or antigen-binding fragment thereof has a Kd between $1.0×10^{−12}$M and $2.5×10^{−11}$M for human DKK-1 (SEQ ID NO: 29), cynomolgus DKK-1 (SEQ ID NO: 30), rat Dkk-1 (SEQ ID NO: 31), mouse DKK-1 (SEQ ID NO: 33), and rabbit DKK-1 (SEQ ID NO: 32). The Kd values are established by a binding equilibrium at 37° C. as described in Example 2.

The present invention provides a human engineered DKK-1 antibody or a binding fragment thereof, comprising a light chain variable region (LCVR) and a heavy chain variable region (HCVR), wherein the LCVR comprises complementarity determining regions (CDRs) LCDR1, LCDR2, and LCDR3 and the HCVR comprises CDRs HCDR1, HCDR2 and HCDR3, wherein LCDR1 has the amino sequence of SEQ ID NO:5, HCDR1 has the amino sequence of SEQ ID NO:1, and HCDR2 has the amino sequence of SEQ ID NO:2.

The present invention provides a human engineered DKK-1 antibody or a binding fragment thereof wherein LCDR1 has the amino sequence of SEQ ID NO:46, LCDR2 has the amino sequence of SEQ ID NO:48, LCDR3 has the amino sequence of SEQ ID NO:50, HCDR1 has the amino sequence of SEQ ID NO:1, HCDR2 has the amino sequence of SEQ ID NO:43, and HCDR3 has the amino sequence of SEQ ID NO:45. The present invention preferably provides a human engineered DKK-1 antibody or a binding fragment thereof wherein LCDR1 has the amino sequence of SEQ ID NO:5, LCDR2 has the amino sequence of SEQ ID NO:47, LCDR3 has the amino sequence of SEQ ID NO:49, HCDR1 has the amino sequence of SEQ ID NO:1, HCDR2 has the amino sequence of SEQ ID NO:2, and HCDR3 has the amino sequence of SEQ ID NO:44.

The present invention provides a human engineered DKK-1 antibody or a binding fragment thereof wherein LCDR1 has the amino sequence of SEQ ID NO:5, LCDR2 has an amino sequence selected from the group consisting of SEQ ID NO:6, SEQ ID NO:8, and SEQ ID NO:10, LCDR3 has an amino sequence selected from the group consisting of SEQ ID NO:7 and SEQ ID NO:9, HCDR1 has the amino sequence of SEQ ID NO:1, HCDR2 has the amino sequence of SEQ ID NO:2, and HCDR3 has an amino sequence selected from the group consisting of SEQ ID NO:3 and SEQ ID NO:4.

The present invention preferably provides a human engineered DKK-1 antibody or antigen-binding fragment thereof wherein LCDR1, LCDR2, LCDR3, HCDR1, HCDR2 and HCDR3 have amino acid sequences selected from the group consisting of:
(i) LCDR1 is SEQ ID NO: 5, LCDR2 is SEQ ID NO: 6, LCDR3 is SEQ ID NO: 7, HCDR1 is SEQ ID NO: 1, HCDR2 is SEQ ID NO: 2, and HCDR3 is SEQ ID NO: 3,
(ii) LCDR1 is SEQ ID NO: 5, LCDR2 is SEQ ID NO: 8, LCDR3 is SEQ ID NO: 7, HCDR1 is SEQ ID NO: 1, HCDR2 is SEQ ID NO: 2, and HCDR3 is SEQ ID NO: 4,
(iii) LCDR1 is SEQ ID NO: 5, LCDR2 is SEQ ID NO: 6, LCDR3 is SEQ ID NO: 9, HCDR1 is SEQ ID NO: 1, HCDR2 is SEQ ID NO: 2, and HCDR3 is SEQ ID NO: 3,
(iv) LCDR1 is SEQ ID NO: 5, LCDR2 is SEQ ID NO: 10, LCDR3 is SEQ ID NO: 9, HCDR1 is SEQ ID NO: 1, HCDR2 is SEQ ID NO: 2, and HCDR3 is SEQ ID NO: 3

The present invention provides a human engineered DKK-1 antibody or antigen-binding fragment thereof wherein the LCVR comprises the amino acid sequence of SEQ ID NO: 52 and the HCVR comprises the amino acid sequence of SEQ ID NO: 51.

The present invention preferably provides a human engineered DKK-1 antibody or antigen-binding fragment thereof wherein the LCVR comprises an amino acid sequence selected from the group consisting of SEQ ID NO:13, SEQ ID NO:14, SEQ ID NO:15, and SEQ ID NO:16.

The present invention preferably provides a human engineered DKK-1 antibody or antigen-binding fragment thereof, wherein the HCVR comprises an amino acid sequence selected from the group consisting of SEQ ID NO:11 and SEQ ID NO:12.

The present invention preferably provides a human engineered DKK-1 antibody or antigen-binding fragment thereof, wherein the LCVR and HCVR comprise amino acid sequences selected from the group consisting of:
(i) a LCVR comprising the amino acid sequence of SEQ ID NO:13 and a HCVR comprising the amino acid sequence of SEQ ID NO:11;
(ii) a LCVR comprising the amino acid sequence of SEQ ID NO:14 and a HCVR comprising the amino acid sequence of SEQ ID NO:12;
(iii) a LCVR comprising the amino acid sequence of SEQ ID NO:15 and a HCVR comprising the amino acid sequence of SEQ ID NO:11;
(iv) a LCVR comprising the amino acid sequence of SEQ ID NO:16 and a HCVR comprising the amino acid sequence of SEQ ID NO:11.

The present invention preferably provides a human engineered DKK-1 antibody or antigen-binding fragment thereof comprising a LCVR comprising the amino acid sequence of SEQ ID NO:14 and a HCVR comprising the amino acid sequence of SEQ ID NO:12.

The present invention preferably provides a human engineered DKK-1 antibody wherein the human engineered DKK-1 antibody comprises a light chain wherein the light chain comprises an amino acid sequence selected from the group consisting of SEQ ID NO:19, SEQ ID NO:20, SEQ ID NO:21, and SEQ ID NO:22.

The present invention preferably provides a human engineered DKK-1 antibody, wherein the human engineered DKK-1 antibody comprises a heavy chain wherein the heavy chain comprises an amino acid sequence selected from the group consisting of SEQ ID NO:17 and SEQ ID NO:18.

More preferably, the present invention provides a human engineered DKK-1 antibody, wherein the human engineered DKK-1 antibody comprises a heavy chain and a light chain amino acid sequence selected from the group consisting of (i) a heavy chain comprising the amino acid sequence of SEQ ID NO:17 and light chain comprising the amino acid sequence of SEQ ID NO:19, (ii) a heavy chain comprising the amino acid sequence of SEQ ID NO:18 and a light chain comprising the amino acid sequence of SEQ ID NO:20, (iii) a heavy chain comprising the amino acid sequence of SEQ ID NO:17 and a light chain comprising the amino acid sequence of SEQ ID NO:21, and (iv) a heavy chain comprising the amino acid sequence of SEQ ID NO:17 and a light chain comprising the amino acid sequence of SEQ ID NO: 22.

The present invention preferably provides a human engineered DKK-1 antibody comprising two light chains wherein each light chain comprises the amino acid sequence of SEQ ID NO: 19, and two heavy chains wherein each heavy chain comprises the amino acid sequence of SEQ ID NO:17.

The present invention preferably provides a human engineered DKK-1 antibody comprising two light chains wherein each light chain comprises the amino acid sequence of SEQ ID NO: 21, and two heavy chains wherein each heavy chain comprises the amino acid sequence of SEQ ID NO:17.

The present invention preferably provides a human engineered DKK-1 antibody comprising two light chains wherein each light chain comprises the amino acid sequence of SEQ ID NO:22, and two heavy chains wherein each heavy chain comprises the amino acid sequence of SEQ ID NO:17.

The present invention preferably provides a human engineered DKK-1 antibody comprising two light chains wherein each light chain comprises the amino acid sequence of SEQ ID NO: 20, and two heavy chains wherein each heavy chain comprises the amino acid sequence of SEQ ID NO:18.

The present invention also provides an antibody or antigen-binding fragment thereof, which competes with the human engineered DKK-1 antibody or antigen-binding fragment thereof of the present invention for binding to human DKK-1 (SEQ ID NO: 29) as determined via an antibody competition assay.

The present invention also provides a pharmaceutical composition comprising the human engineered DKK-1 antibody or antigen-binding fragment thereof of the present invention and a pharmaceutically acceptable carrier, diluent, or excipient.

Furthermore, the present invention provides a pharmaceutical composition comprising the human engineered DKK-1 antibody or antigen-binding fragment thereof of the present invention together with a pharmaceutically acceptable carrier, diluent, or excipient and optionally other therapeutic ingredients.

In a further aspect, the present invention provides a method of healing bone comprising administering a human engineered DKK-1 antibody or antigen binding fragment thereof of the present invention.

In a further aspect, the present invention provides a method of treating cancer comprising administering a human engineered DKK-1 antibody or antigen binding fragment thereof of the present invention, wherein the cancer is preferably selected from the group consisting of multiple myeloma, breast cancer and non-small cell lung cancer.

Furthermore, the present invention provides a human engineered DKK-1 antibody or antigen binding fragment thereof of the present invention for use in therapy. Preferably, the present invention provides a human engineered DKK-1 antibody or antigen binding fragment thereof of the present invention for use in the treatment for healing bone or in the treatment of cancer, wherein the cancer is preferably selected from the group consisting of multiple myeloma, breast cancer and non-small cell lung cancer.

Furthermore, the present invention also provides for the use of a human engineered DKK-1 antibody or antigen binding fragment thereof of the present invention in the manufacture of a medicament for therapy, healing bone or to treat cancer, wherein the cancer is preferably selected from the group consisting of multiple myeloma, breast cancer and non-small cell lung cancer.

DEFINITIONS

A full-length antibody as it exists naturally is an immunoglobulin molecule comprising 2 heavy (H) chains and 2 light (L) chains interconnected by disulfide bonds. The amino terminal portion of each chain includes a variable region of about 100-110 amino acids primarily responsible for antigen recognition via the complementarity determining regions (CDRs) contained therein. The carboxy-terminal portion of each chain defines a constant region primarily responsible for effector function.

The CDRs are interspersed with regions that are more conserved, termed framework regions ("FR"). Each light chain variable region (LCVR) and heavy chain variable region (HCVR) is composed of 3 CDRs and 4 FRs, arranged from amino-terminus to carboxy-terminus in the following order: FR1, CDR1, FR2, CDR2, FR3, CDR3, FR4. The 3 CDRs of the light chain are referred to as "LCDR1, LCDR2, and LCDR3" and the 3 CDRs of the heavy chain are referred to as "HCDR1, HCDR2, and HCDR3." The CDRs contain most of the residues which form specific interactions with the antigen. The numbering and positioning of CDR amino acid residues within the LCVR and HCVR regions is in accordance with the well-known Kabat numbering convention.

Light chains are classified as kappa or lambda, and are characterized by a particular constant region as known in the art. Heavy chains are classified as gamma, mu, alpha, delta, or epsilon, and define the isotype of an antibody as IgG, IgM, IgA, IgD, or IgE, respectively. IgG antibodies can be further divided into subclasses, e.g., IgG1, IgG2, IgG3, IgG4. Each heavy chain type is characterized by a particular constant region with a sequence well known in the art.

As used herein, the term "monoclonal antibody" (Mab) refers to an antibody that is derived from a single copy or clone including, for example, any eukaryotic, prokaryotic, or phage clone, and not the method by which it is produced. Mabs of the present invention preferably exist in a homogeneous or substantially homogeneous population. Complete Mabs contain 2 heavy chains and 2 light chains. "Antigen-binding fragments" of such monoclonal antibodies include, for example, Fab fragments, Fab' fragments, F(ab')$_2$ fragments, and single chain Fv fragments. Monoclonal antibodies and antigen-binding fragments thereof of the present invention can be produced, for example, by recombinant technologies, phage display technologies, synthetic technologies, e.g., CDR-grafting, or combinations of such technologies, or other technologies known in the art. For example, mice can be immunized with human DKK-1 or fragments thereof, the resulting antibodies can be recovered and purified, and determination of whether they possess binding and functional properties similar to or the same as the antibody compounds disclosed herein can be assessed by the methods disclosed in Examples below. Antigen-binding fragments can also be prepared by conventional methods. Methods for producing and purifying antibodies and antigen-binding fragments are well known in the art and can be found, for example, in Harlow and Lane (1988) *Antibodies, A Laboratory Manual*, Cold Spring Harbor Laboratory Press, Cold Spring Harbor, N.Y., chapters 5-8 and 15, ISBN 0-87969-314-2.

The phrase "chimeric antibody" refers to an antibody containing domains from different species (generally 2 species). Antibody V is a chimeric antibody wherein the light chain and heavy chain variable domains contain residues from a murine antibody, whereas the constant region light chain domain contains residues comprising a rat kappa light chain and the constant region heavy chain domains contains residues comprising a rat IgG1 antibody. Antibody V is a murine/rat chimera and is used in studies to reduce the likelihood of immune response in long-term pre-clinical models.

The phrase "human engineered antibodies" refers to monoclonal antibodies that have binding and functional properties according to the invention, and that have framework regions that are substantially human or fully human surrounding CDRs derived from a non-human antibody. "Antigen-binding fragments" of such human engineered antibodies include, for example, Fab fragments, Fab' fragments, F(ab')$_2$ fragments, and single chain Fv fragments. "Framework region" or "framework sequence" refers to any one of framework regions 1 to 4. Human engineered antibodies and antigen-binding fragments thereof encompassed by the present invention include molecules wherein any one or more of framework regions 1 to 4 is substantially or fully human, i.e., wherein any of the possible combinations of individual substantially or fully human framework regions 1 to 4, is present. For example, this includes molecules in which framework region 1 and framework region 2, framework region 1 and framework region 3, framework region 1, 2, and 3, etc., are substantially or fully human. Substantially human frameworks are those that have at least about 80% sequence identity to a known human germline framework sequence. Preferably, the substantially human frameworks have at least about 85%, about 90%, about 95%, or about 99% sequence identity to a known human germline framework sequence.

Fully human frameworks are those that are identical to a known human germline framework sequence. Human framework germline sequences can be obtained from ImMunoGeneTics (IMGT) via their website http://imgt.cines.fr, or from *The Immunoglobulin Facts Book* by Marie-Paule Lefranc and Gerard Lefranc, Academic Press, 2001, ISBN 012441351. For example, germline light chain frameworks can be selected from the group consisting of: A11, A17, A18, A19, A20, A27, A30, LI, L1I, L12, L2, L5, L15, L6, L8, O12, O2, and O8, and germline heavy chain framework regions can be selected from the group consisting of: VH2-5, VH2-26, VH2-70, VH3-20, VH3-72, VHI-46, VH3-9, VH3-66, VH3-74, VH4-31, VHI-18, VHI-69, VI-13-7, VH3-11, VH3-15, VH3-21, VH3-23, VH3-30, VH3-48, VH4-39, VH4-59, and VH5-5I.

Human engineered antibodies in addition to those disclosed herein exhibiting similar functional properties according to the present invention can be generated using several different methods. The specific antibody compounds disclosed herein can be used as templates or parent antibody compounds to prepare additional antibody compounds. In one approach, the parent antibody compound CDRs are grafted into a human framework that has a high sequence identity with the parent antibody compound framework. The sequence identity of the new framework will generally be at least about 80%, at least about 85%, at least about 90%, at least about 95%, or at least about 99% identical to the sequence of the corresponding framework in the parent antibody compound. This grafting may result in a reduction in binding affinity compared to that of the parent antibody. If this is the case, the framework can be back-mutated to the parent framework at certain positions based on specific criteria disclosed by Queen et al. (1991) *Proc. Natl. Acad. Sci. USA* 88:2869. Additional references describing methods useful in humanizing mouse antibodies include U.S. Pat. Nos. 4,816,397; 5,225,539, and 5,693,761; computer programs ABMOD and ENCAD as described in Levitt (1983) *J. Mol. Biol.* 168:595-620; and the method of Winter and co-workers (Jones et al. (1986) *Nature* 321:522-525; Riechmann et al. (1988) *Nature* 332:323-327; and Verhoeyen et al. (1988) *Science* 239:1534-1536.

The identification of residues to consider for back-mutation can be carried out as follows:

When an amino acid falls under the following category, the framework amino acid of the human germ-line sequence that is being used (the "acceptor framework") is replaced by a framework amino acid from a framework of the parent antibody compound (the "donor framework"):

(a) the amino acid in the human framework region of the acceptor framework is unusual for human frameworks at that position, whereas the corresponding amino acid in the donor immunoglobulin is typical for human frameworks at that position;

(b) the position of the amino acid is immediately adjacent to one of the CDRs; or (c) any side chain atom of a framework amino acid is within about 5-6 angstroms (center-to-center) of any atom of a CDR amino acid in a three dimensional immunoglobulin model.

When each of the amino acids in the human framework region of the acceptor framework and a corresponding amino acid in the donor framework is generally unusual for human frameworks at that position, such amino acid can be replaced by an amino acid typical for human frameworks at that position. This back-mutation criterion enables one to recover the activity of the parent antibody compound.

Another approach to generating human engineered antibodies exhibiting similar functional properties to the antibody compounds disclosed herein involves randomly mutating amino acids within the grafted CDRs without changing the framework, and screening the resultant molecules for binding affinity and other functional properties that are as good as or better than those of the parent antibody compounds. Single mutations can also be introduced at each amino acid position within each CDR, followed by assessing the effects of such mutations on binding affinity and other functional properties. Single mutations producing improved properties can be combined to assess their effects in combination with one another.

Further, a combination of both of the foregoing approaches is possible. After CDR grafting, one can back-mutate specific framework regions in addition to introducing amino acid changes in the CDRs. This methodology is described in Wu et al. (1999) *J. Mol. Biol.* 294:151-162.

Applying the teachings of the present invention, a person skilled in the art can use common techniques, e.g., site-directed mutagenesis, to substitute amino acids within the presently disclosed CDR and framework sequences and thereby generate further variable region amino acid sequences derived from the present sequences. All alternative naturally occurring amino acids can be introduced at a specific substitution site. The methods disclosed herein can then be used to screen these additional variable region amino acid sequences to identify sequences having the indicated in vivo functions. In this way, further sequences suitable for preparing human engineered antibodies and antigen-binding portions thereof in accordance with the present invention can be identified. Preferably, amino acid substitution within the frameworks is restricted to one, two, or three positions within any one or more of the 4 light chain and/or heavy chain framework regions disclosed herein. Preferably, amino acid substitution within the CDRs is restricted to one, two, or three positions within any one or more of the 3 light chain and/or heavy chain CDRs. Combinations of the various changes within these framework regions and CDRs described above are also possible. Most preferably, these techniques are used to generate further variable region amino acid sequences using the variable heavy and light chain amino acid sequences describes in SEQ ID NO:12 and SEQ ID NO:14 respectively.

Human engineered antibodies or antigen-binding fragments thereof that "compete" with the molecules disclosed herein are those that bind human DKK-1 (SEQ ID NO:29) at site(s) that are identical to, or overlapping with, the site(s) at which the present molecules bind. Competing human engineered antibodies or antigen-binding fragments thereof can be identified, for example, via an antibody competition assay. For example, a sample of purified or partially purified human DKK-1 (SEQ ID NO:29) is bound to a solid support. An antibody disclosed herein and a test monoclonal antibody or antigen-binding fragment, with either the test or antibody of the present invention labeled, are then added. If the labeled antibody and the unlabeled antibody bind to separate and discrete sites on DKK-1, the labeled antibody will bind to the same level whether or not the suspected competing antibody is present. However, if the sites of interaction are identical or overlapping, the unlabeled antibody will compete, and the amount of labeled antibody bound to the antigen will be lowered. If the unlabeled antibody is present in excess, no labeled antibody will bind. For purposes of the present invention, competing human engineered antibodies or antigen-binding fragments thereof are those that decrease the binding of the present antibodies to DKK-1 by about 50%, about 60%, about 70%, about 80%, about 85%, about 90%, about 95%, or about 99%. Details of procedures for carrying out such competition assays are well known in the art and can be found, for example, in Harlow and Lane (1988) *Antibodies, A Laboratory Manual*, Cold Spring Harbor Laboratory Press, Cold Spring Harbor, N.Y., pages 567-569, ISBN 0-87969-314-2. Such assays can be made quantitative by using purified antibodies. A standard curve is established by titrating one antibody against a labeled version of itself. The capacity of an unlabeled competing monoclonal antibody or antigen-binding fragment thereof to inhibit the binding of the labeled molecule to the plate is titrated. The results are plotted, and the concentrations necessary to achieve the desired degree of binding inhibition are compared. Whether monoclonal antibodies or antigen-binding fragments thereof that compete with human engineered antibodies or antigen-binding fragments thereof of the present invention in such competition assays possess the same or similar functional properties of the present human engineered antibodies can be determined via the methods disclosed in Examples herein.

The term "inhibit" means the ability to substantially antagonize, prohibit, prevent, restrain, slow, disrupt, eliminate, stop, reduce, or reverse the biological effects of DKK-1.

The term "treating" (or "treat" or "treatment") refers to processes involving a slowing, interrupting, arresting, controlling, stopping, reducing, or reversing the progression or severity of a symptom, disorder, condition, or disease, but does not necessarily involve a total elimination of all disease-related symptoms, conditions, or disorders associated with DKK-1 activity.

The term "preventing" (or "prevent" or "prevention") means prohibiting, restraining, or inhibiting the incidence or occurrence of a symptom, disorder, condition, or disease. Acute events and chronic conditions may be treated and prevented. In an acute event, an antibody or antigen-binding fragment thereof is administered at the onset of a symptom, disorder, condition, or disease, and is discontinued when the acute event ends. In contrast, a chronic symptom, disorder, condition, or disease is treated over a more protracted time frame.

The term "effective amount" refers to the amount or dose of an antibody compound of the present invention which, upon single or multiple dose administration to a patient, provides the desired treatment or prevention. Therapeutically effective amounts of the present antibody compounds can comprise an amount in the range of from about 0.1 mg/kg to about 20 mg/kg per single dose. A therapeutically effective amount for any individual patient can be determined by the health care provider by monitoring the effect of the antibody compounds on a biomarker.

The term "bone healing" refers to the stimulation of bone formation at sites of injury by blocking DKK-1. Examples of bone healing indications include, but are not limited to, fracture healing, implant fixation/retention, and dental implant fixation/retention.

The human engineered antibodies of the present invention can be used as medicaments in human medicine, administered by a variety of routes. Most preferably, such compositions are for parenteral administration. Such pharmaceutical compositions can be prepared by methods well known in the art (See, e.g., *Remington: The Science and Practice of Pharmacy*, 19$^{th}$ ed. (1995), A. Gennaro et al., Mack Publishing Co.) and comprise a human engineered antibody as disclosed herein, and a pharmaceutically acceptable carrier, diluent, or excipient.

The results of the following assays demonstrate that the monoclonal antibodies and antigen-binding fragments thereof, of the present invention are useful as a DKK-1 inhibitor. The antibodies of the present invention possess a number of desirable properties. For example, Antibody II of the present invention has increased chemical and physical stability, and solubility. Accelerated studies are performed to assess the chemical stability of antibodies by incubating the antibodies of the present invention under different buffer conditions (pH and NaCl variation) and incubating at 4° C., 25° C., and 40° C. for 4 weeks. Chemical modifications of the antibodies of the present invention are detected by cation-exchange ("CEX") chromatography to separate charge variants (eg., deamidation of asparagine to aspartic acid) and LC-MS analysis to identify specific sites of degradation. Antibody II has the least amount of degradation detected by CEX and this result is further confirmed by LC-MS data showing that all three asparagine residues in the CDRs had the least amount of deamidation compared to the other antibodies described herein after 4-week incubation at 40° C. in pH 8 buffer. Solubility for Antibody II is more favorable compared to Antibody I when formulated at pH 6+150 mM NaCl. Furthermore, Antibody II maintained solubility of >105 mg/mL when stored in 4° C., whereas solubility for Antibody I is only 48 mg/mL and precipitated under these same conditions. As used herein, "EC50" refers to the concentration of an agent which produces 50% of the maximal response possible for that agent. "Kd" refers to the equilibrium dissociation constant which can be calculated by the formula: $k_{off}/k_{on}=Kd$.

EXAMPLE 1

Production of Antibodies

Antibodies I, II, III, and IV can be made and purified as follows. An appropriate host cell, such as HEK 293 EBNA or CHO, is either transiently or stably transfected with an expression system for secreting antibodies using an optimal predetermined HC:LC vector ratio or a single vector system encoding both HC, such as SEQ ID NO: 23, or SEQ ID NO: 24, and LC, such as SEQ ID NO: 25, SEQ ID NO: 26, SEQ ID NO: 27, or SEQ ID NO: 28. Clarified media, into which the antibody has been secreted, is purified using any of many commonly-used techniques. For example, the medium may be conveniently applied to a Protein A or G Sepharose FF column that has been equilibrated with a compatible buffer, such as phosphate buffered saline (pH 7.4). The column is washed to remove nonspecific binding components. The bound antibody is eluted, for example, by pH gradient (such as 0.1 M sodium phosphate buffer pH 6.8 to 0.1 M sodium citrate buffer pH 3.0). Antibody fractions are detected, such as by SDS-PAGE, and then are pooled. Further purification is optional, depending on the intended use. The antibody may be concentrated and/or sterile filtered using common techniques. Soluble aggregate and multimers may be effectively removed by common techniques, including size exclusion, hydrophobic interaction, ion exchange, or hydroxyapatite chromatography. The purity of the antibody after these chromatography steps is greater than 99%. The product may be immediately frozen at −70° C. or may be lyophilized. The amino acid sequences for these antibodies are provided below.

| SEQ ID NOs | | | | |
|---|---|---|---|---|
| Antibody | Heavy Chain | Light Chain | HCVR | LCVR |
| I | 17 | 19 | 11 | 13 |
| II | 18 | 20 | 12 | 14 |
| III | 17 | 21 | 11 | 15 |
| IV | 17 | 22 | 11 | 16 |
| V | 35 | 34 | 37 | 36 |

| Antibody | HCDR1 | HCDR2 | HCDR3 | LCDR1 | LCDR2 | LCDR3 |
|---|---|---|---|---|---|---|
| I | 1 | 2 | 3 | 5 | 6 | 7 |
| II | 1 | 2 | 4 | 5 | 8 | 7 |
| III | 1 | 2 | 3 | 5 | 6 | 9 |
| IV | 1 | 2 | 3 | 5 | 10 | 9 |
| V | 1 | 38 | 39 | 40 | 41 | 42 |

EXAMPLE 2

Affinity (Kd) Measurements for DKK-1 Antibodies

To establish a binding equilibrium, a constant concentration of antibody is mixed with varying concentrations of His-tagged DKK-1 (SEQ ID NO:29, SEQ ID NO:30, SEQ ID NO:31, SEQ ID NO:32, or SEQ ID NO:33) (1 nM-1 pM range) in PBS (pH 7.4)+1 mg/mL bovine serum albumin ("BSA") or buffer alone and incubated for several days at 37° C. Two sets of binding reactions are set up, one set at low concentration of antibody (3 pM) and one set at high concentration of antibody (30 or 50 pM).

After establishing equilibrium, a KinExA 3000 instrument (Sapidyne Inst. Inc.) is used to probe for the fraction of 'free' (unbound) antibody. Briefly, His-tagged DKK-1 is covalently coupled to NHS-activated Sepharose 4 Fast Flow beads (GE Healthcare) which are packed by the instrument to create a small column. The pre-equilibrated mixtures of antibody+ His-tagged DKK-1 are passed over the beads to capture only free antibody. The amount of free antibody captured is proportional to the free concentration in the equilibrated samples, and is detected by injection of a fluorescently labeled secondary antibody. Data sets from low and high concentrations of antibody are fit globally using n-curve analysis in the KinExA software. This fitting returns a Kd value as well as the 95% confidence interval.

TABLE 1

Antibody II affinity to DKK-1 from various species

| DKK-1 Species | Kd (pM) | 95% Confidence Interval for Kd (pM) |
|---|---|---|
| Human | 3.3 | 1.4-7.5 |
| Cynomolgus | 14 | 8.4-26 |
| Rat | 8.4 | 3.9-23 |
| Murine | 7.0 | 4.7-11 |
| Rabbit | 17 | 11-27 |

EXAMPLE 3

Effect of Dkk-1 Antibodies in C2C12 Alkaline Phosphatase Assay

Canonical Wnt signaling is important for osteoblast differentiation and activity. Wnt-3a CM (Conditioned Media) combined with BMP-4 induces pluripotent mouse C2C12 cells to differentiate into osteoblasts with a measurable endpoint of alkaline phosphatase ("AP"), a marker of osteoblast activity. DKK-1, an inhibitor of canonical Wnt signaling, inhibits the differentiation and production of AP. Neutralizing DKK-1 antibodies prevent DKK-1-mediated inhibition of AP. Antibodies which block DKK-1 inhibitory activity prevent the loss of AP activity.

C2C12 cells are grown to 60%-80% confluence in tissue culture flasks in growth medium (Dulbecco's Modified Eagle's Medium ("DMEM") containing L-glutamine, 10% heat-inactivated fetal bovine serum ("FBS"), 1× antibiotic/antimycotic, 1× sodium pyruvate). C2C12 cells are resuspended to a concentration of 30,000 cells/mL in growth medium and 100 μL/well are added to a 96-well tissue culture plate and incubated overnight at 37° C., 95% humidity, 5% $CO_2$. Growth medium is replaced with 50 μL assay medium (DMEM containing L-glutamine, 5% heat-inactivated FBS, 1× antibiotic/antimycotic, 1× sodium pyruvate). To stimulate differentiation (and thus induce AP production), 100 μL assay medium plus 1.5×Wnt-3a CM+BMP-4 (R & D Systems catalogue #314-BP) are added. This yields a final concentration of 1× Wnt-3a CM and 25 ng/mL BMP-4. Negative controls contain only L-cell CM (no Wnt-3a or BMP-4). Cells are incubated at 37° C., 95% humidity, 5% $CO_2$ for 72 hours. Medium is removed, cells are washed with 200 μL phosphate-buffered saline ("PBS"), and the PBS is removed. Cells are freeze-thawed 3 times. 100 μL One-step pNPP substrate (Thermo Scientific catalogue #37621) is added per well, and the plate is incubated at room temperature. Absorbance is read at 405 nm. To determine the concentration of DKK-1 required to inhibit differentiation, Dkk-1 molecules from various species are titrated to identify the minimal concentration required to fully inhibit AP induction.

The minimal concentration of DKK-1 from each species which fully inhibits AP induction is as follows: human DKK-1=38 nM, cynomolgus DKK-1=11.4 nM, rat DKK-1=5.8 nM, and rabbit DKK-1=25.0 nM.

Having determined the concentration of DKK-1 which fully inhibits AP induction, increasing concentrations of an anti-DKK-1 antibody are pre-incubated in assay medium with an inhibitory concentration of Dkk-1 for 30 minutes at room temperature. AP induction is determined as described above. Results are reported as an EC50 (nM±standard error).

Antibody II blocks Dkk-1-mediated inhibition of C2C12 AP. For the DKK-1 of various species, the EC50's (given as nM±standard error) are as follows: human=9.8±0.41, cynomolgus=6.4±0.25, rat=2.9±0.25, and rabbit=6.0±0.32.

EXAMPLE 4

Cortical Defect (CD) in Vivo Assay

Six month old female Sprague-Dawley rats are ovariectomized and allowed to lose bone for two months. 2 mm diameter defects are introduced into the left and right femurs with an electric drill with a 2 mm dental bit. This hole extends through both the anterior and posterior cortices. Healing of bone is monitored longitudinally by assessing bone mass density ("BMD") through the use of quantitative computed tomography ("qCT") for 35 days after surgery. At the end of the experiment, animals are sacrificed and whole femora are subjected to loaded-to-failure determinations to ascertain biomechanical strength of the whole diaphysis. Antibodies are administered subcutaneously at doses and intervals as indicated.

Antibody II is dosed as follows: 5 mg/kg once every two weeks starting one day after surgery (Group 1), 1 mg/kg (Group 2), 5 mg/kg (Group 3), or 15 mg/kg (Group 4) is administered once every two weeks starting nine days after surgery. BMD is assessed by qCT at day 35. Group 1 showed a statistically significant increase in BMD at both the anterior and posterior cortices. Group 4 showed a statistically significant increase in BMD at both cortices, although Groups 2 and 3 showed a non-significant increase in BMD.

EXAMPLE 5

Cancer in Vivo Efficacy Assay

Mice (female C.B-17 mice, Fox Chase severe combined immunodeficient model #CB17SC-M) are acclimated for one week in an animal facility prior to experiment initiation. After acclamation, mice are randomized into groups of 10 per treatment. Cultured human A549 non-small cell lung carcinoma cells are implanted subcutaneously in the rear flank of the mice and tumor are allowed to reach a mean tumor volume ~100 mm3. Antibody II (1 mg/kg and 5 mg/kg), control IgG antibody (1 mg/kg and 5 mg/kg), or vehicle (citrate buffered saline supplemented with 0.02% Tween 80) is administered via subcutaneous injection. Animals receive 2 treatments separated by 7 days.

The tumors are measured 2 times per week by electronic calipers to plot growth curves. Animals are also monitored twice a week for fluctuations in body weight and signs of toxicity. Tumor volume measurements shown in table 3 are taken on day 29.

As shown in Table 2, treatment groups receiving Antibody II, demonstrated significant growth inhibition of human A549 non-small cell lung xenografts in vivo.

TABLE 2

Efficacy of Antibody II in A549 human non-small cell lung carcinoma xenograft model

| Treatment Group | Tumor Volume ± Standard Error (mm3) | p-Value (relative to vehicle control group) |
| --- | --- | --- |
| Citrate vehicle | 402 ± 36 | — |
| IgG control (1 mg/kg) | 372 ± 45 | — |
| IgG control (5 mg/kg) | 492 ± 72 | — |
| Antibody II (1 mg/kg) | 279 ± 32 | 0.01-0.05 |
| Antibody II (5 mg/kg) | 202 ± 21 | <0.001 |

EXAMPLE 6

Angiogenic Re-Normalization in Vivo Xenograft Assay

To understand the mechanism of the anti-tumor efficacy, high content imaging analysis is carried out on A549 tumors treated with Antibody II or IgG control. Several phenotypic-based markers are analyzed both quantitatively and qualitatively to assess the cancer-relevant biological processes of angiogenesis (CD31 and smooth muscle actin, SMA), hypoxia induction (Glucose transporter 1, GLUT1), cell proliferation (Ki67), and apoptosis (Terminal UDP Nick-End Labeling, TUNEL).

Female C.B-17 (Fox Chase SCID) model #CB17SC-M mice age 7 to 8 weeks old are acclimated for one week and allowed to feed ad libitum on a normal low fat (4.5%) diet, which is continued for the duration of the study.

A549 cells from ATCC origin are grown and divided in F-12 Kaighn's media (InVitrogen #21127) supplemented with 10% FBS (InVitrogen #0, and 100× dilutions of sodium pyruvate, non-essential amino acids and pen-strep (Invitrogen #11360, #11140 and #15140 respectively). They are detached and prepared at a final concentration of $50 \times 10^6$ cells/ml in PBS at passage 19 with 95% viability.

$5 \times 10^6$ A549 human lung carcinoma cells are injected subcutaneously in the flank of subject mice in a 1:1 mixture of PBS and Matrigel (Becton Dickinson, Bedford, Mass.). Tumor and body weight measurements are performed twice weekly. Prior to treatment, mice are randomized based on tumor size using a randomization algorithm.

Starting when tumors reached 200 mm$^3$, the randomized mice are separated into 2 groups of 10 animals and dosed subcutaneously on day 1 and again on day 8 with 5 mg/kg of either Antibody II or the IgG4 control. The study is terminated 10 days after administration of the first dose of antibody.

Antibody II is prepared in Citrate Buffered Saline (CBS) (10 mM citrate pH6, 150 mM NaCl and 0.2% polysorbate). IgG4 control is provided at 6.0 mg/ml in Phosphate Buffered Saline (PBS).

Xenograft tumors are excised from mice after 17 days of dosing and placed into Zinc-Tris fixative (BD Pharmingen). Fixed tumors are processed, blocked in paraffin, and sectioned as 3 µM slices onto standard microscope slides. Slides are baked at 60° F. for 1 hour and then deparaffinized in xylene (4 treatments, 10 minutes each). Slides are rehydrated through a series of ethanol/water immersions with final washes in Tris-buffered saline/Tween (TBST). Slides are then blocked with Protein Block (DAKO) for 30 minutes. For the Tumor Health Panel, slides are stained with a combination of Hoechst 33324 (Invitrogen), rat anti-human CD31 (Pharmingen)/anti-rat Alexa-488 (Invitrogen), rabbit anti-Ki67 (Neo-Markers)/anti-rabbit Alexa 647 (Invitrogen), and TUNEL-TMR red (diluted 1:5 in TUNEL dilution buffer; Roche). For the Angiogenesis Panel, slides are stained with a combination of Hoechst 33324 (Invitrogen), rat anti-human CD31 (Pharmingen)/anti-rat Alexa-488 (Invitrogen), rabbit anti-GLUT1 (Chemicon)/anti-rabbit Alexa 647 (Invitrogen), and mouse anti-Smooth Muscle Actin/Cy3 (Sigma). Slides are imaged using an iCys Laser Scanning Cytometer (CompuCyte) and a Marianas Digital Imaging Workstation configured with a Zeiss Axiovert 200M inverted fluorescence microscope (Intelligent Imaging Innovations). Quantitative data comparisons of treatment groups are performed using the Dunnet's analysis in JMP statistics software (SAS).

As shown in Table 3, A549 xenografts from control IgG-treated animals are modestly vascularized, have moderate levels of myofibroblasts and many focalized areas of hypoxia. Control IgG-treated tumors have an extended network of vessels consisting of both neoangiogenic vascular sprouts and mature vessels that are poorly covered by pericytes. Control IgG-treated tumors have hypoxic areas (marked by GLUT 1) that are clearly demarcated zones some distance from perfused vessels and necrotic areas that are even further from vessels. Treatment with Antibody II results in decreased vessel area, decreased pericyte area, and decreased pericyte coverage of vessels. However, this treatment did not result in a significant difference in tumor hypoxia. Qualitatively, the Antibody II-treated tumor vasculature appears to consist of smaller, less-networked vessels and with less pericyte coverage compared with the control IgG-treated group.

As shown in Table 3, IgG-treated tumors have proliferating tumor cells evenly distributed throughout, but also frequently display one or more large areas of necrosis that are avascular. Treatment with Antibody II results in no change in apoptosis and only a slight, non-significant decrease in total proliferation area. However, there is a profound decrease in the percentage of area of high-intensity Ki67 cells in the Antibody II-treated tumors, which could indicate a decreased amount of cells in the G2 cell cycle phase.

TABLE 3

Antibody II in angiogenic re-normalization in vivo xenograft assay

| Phenotypic Panel | Biological Parameter | Control IgG Value: Antibody II Treatment Value | Statistical Significance (Dunnet's p-value) |
|---|---|---|---|
| Tumor Angiogenesis Panel | % Total Vessel Area | 10.26:7.88 | 0.001 |
| Tumor Angiogenesis Panel | % Functional Vessel Area | 9.84:7.59 | 0.0009 |
| Tumor Angiogenesis Panel | % Non-Functional Vessel Area | 0.42:0.30 | 0.1341 |
| Tumor Angiogenesis Panel | % Pericyte Covered Vessels | 42.44:30.88 | 0.0234 |
| Tumor Angiogenesis Panel | % Tumor Hypoxic Area | 14.90:11.77 | 0.3615 |
| Tumor Proliferation Panel | % Tumor Proliferation Area | 12.16:9.68 | 0.1739 |
| Tumor Proliferation Panel | % High Ki67 Area | 0.66:0.19 | 0.0012 |
| Tumor Proliferation Panel | % Cycling Tumor Cells with High Ki67 | 5.24:1.68 | <0.0001 |
| Tumor Apoptosis Panel | % Tumor Apoptosis Area | 8.63:8.24 | 0.7466 |

% Total Vessel Area - Percentage of tumor tissue area covered by all vessels regardless of their functional status.
% Functional Vessel Area - Percentage of tumor tissue area covered by vessels in non-hypoxic regions.
% Non-Functional Vessel Area - Percentage of tumor tissue area covered by vessels in hypoxic regions.
% Pericyte Covered Vessels - Percentage of all tumor vessels that are associated with smooth muscle actin (SMA)-expressing cells.
% Tumor Hypoxic Area - Percentage of tumor tissue area covered by cells expressing GLUT1, a surrogate marker for hypoxia.
% Tumor Proliferation Area - Percentage of tumor tissue area that is positive for Ki67, a nuclear protein routinely used as a marker of actively proliferating cells.
% High Ki67 Area - Percentage of tumor tissue area that stains intensely for Ki67. Cells expressing high levels of Ki67 are in later phases of cell cycle than those that express lower levels of Ki67.
% Cycling Tumor cells with High Ki67 - Percentage of all Ki67 positive cells that are designated as having a high level of Ki67 expression. Cells expressing high levels of Ki67 are in later phases of cell cycle than those that express lower levels of Ki67.
% Tumor Apoptosis Area - Percentage of tumor tissue area with high TUNEL staining. TUNEL is a routinely used method to detect double-stranded DNA breakages which is indicative of terminal apoptosis.

EXAMPLE 7

Bone in Vivo Efficacy Assay

To evaluate the ability of Antibody V (Light chain SEQ ID NO:34 and Heavy chain SEQ ID NO:35) accelerating the peri-implant bone formation and regenerating bone tissue, four months old male Sprague-Dawley rats (Harlan Sprague Dawley Inc) weighting around 425 gram are utilized. Rats are surgically implanted with titanium screw (2 mm×4 mm) into the both legs of the media lateral side right above the tibial-fibular junction. Rats then are randomly divided into 2 groups according the body weight and receive either Antibody V 10 mg/kg or IgG control 10 mg/kg subcutaneously injection once weekly starting the same day of the surgery for 21 days. Quantitative computed tomography (Aloka LaTheta LTC-100 model CT scanner) is used to ex vivo scan and quantify the newly formed bone with a 60-µm voxel size. Volume of interest (VOI) is defined as 28 slices at 0.1 mm interval over the previous implant site. Group differences are assessed with JMP version 5.1. software (Cary, N.C.), comparison against IgG-control using Dunnett's Method with a significance level of P<0.05. Qualitatively evaluation by ex vivo faxitron x-ray images indicates that Antibody V treated rats have more new bone or callus around the implant. Quantitative CT analyses reveal a statistically significant increase cortical peri-implant bone mineral content (14%), new bone area (16%), cortical thickness (7%) and bone marrow cancellous peri-implant new bone mineral content (18%), and bone area (16%) in Antibody V treated rats when compared to IgG control. The data demonstrate that Antibody V stimulates new bone formation and accelerate regenerating bone tissue in titanium implanted rats.

TABLE 4

Micro-CT analyses of Peri-implant New Bone Formation

| Group | n | Bone Marrow Peri-implant Analyses | | Cortical Peri-implant Analyses | | |
|---|---|---|---|---|---|---|
| | | Bone mineral Content (mg) | Bone Area (cm^2) | Bone mineral Content (mg) | Bone Area (cm^2) | Cortical thickness (cm) |
| IgG control | 10 | 0.84 ± 0.04 | 0.034 ± 0.001 | 6.70 ± 0.07 | 0.064 ± 0.001 | 0.054 ± 0.001 |
| Antibody V | 10 | 1.00 ± 0.04* | 0.039 ± 0.002* | 7.61 ± 0.06* | 0.074 ± 0.001* | 0.057 ± 0.001* |

Data are presented as Mean ± SE.
* $p < 0.05$, vs IgG control, JMP Dunnett's test.

We claim:

1. A human engineered DKK-1 antibody or antigen binding fragment thereof, comprising a light chain variable region (LCVR) and a heavy chain variable region (HCVR), wherein the LCVR comprises complementarity determining regions (CDRs) LCDR1, LCDR2, and LCDR3 and the HCVR comprises CDRs HCDR1, HCDR2 and HCDR3, wherein LCDR1 has the amino sequence of SEQ ID NO:5, LCDR2 has the amino sequence of SEQ ID NO:47, LCDR3 has the amino sequence of SEQ ID NO:49, HCDR1 has the amino sequence of SEQ ID NO:1, HCDR2 has the amino sequence of SEQ ID NO:2, and an HCDR3 has the amino sequence of SEQ ID NO:44.

2. The human engineered DKK-1 antibody of claim 1, wherein the LCVR comprises the amino acid sequence of SEQ ID NO: 52 and the HCVR comprises the amino acid sequence of SEQ ID NO: 51.

3. The human engineered DKK-1 antibody of claim 2, wherein the LCVR and HCVR comprise amino acid sequences selected from the group consisting of:
   (i) a LCVR comprising the amino acid sequence of SEQ ID NO: 13 and a HCVR comprising the amino acid sequence of SEQ ID NO: 11;
   (ii) a LCVR comprising the amino acid sequence of SEQ ID NO: 14 and a HCVR comprising the amino acid sequence of SEQ ID NO: 12;
   (iii) a LCVR comprising the amino acid sequence of SEQ ID NO: 15 and a HCVR comprising the amino acid sequence of SEQ ID NO: 11;
   (iv) a LCVR comprising the amino acid sequence of SEQ ID NO: 16 and a HCVR comprising the amino acid sequence of SEQ ID NO: 11.

4. The human engineered DKK-1 antibody of claim 3, wherein the LCVR comprises the amino acid sequence of SEQ ID NO: 14 and the HCVR comprises the amino acid sequence of SEQ ID NO: 12.

5. The human engineered DKK-1 antibody of claim 3, wherein the human engineered DKK-1 antibody comprises a heavy chain and a light chain amino acid sequence selected from the group consisting of
   a. a heavy chain comprising the amino acid sequence of SEQ ID NO: 17 and light chain comprising the amino acid sequence of SEQ ID NO: 19,
   b. a heavy chain comprising the amino acid sequence of SEQ ID NO: 18 and a light chain comprising the amino acid sequence of SEQ ID NO: 20,
   c. a heavy chain comprising the amino acid sequence of SEQ ID NO: 17 and a light chain comprising the amino acid sequence of SEQ ID NO: 21, and
   d. a heavy chain comprising the amino acid sequence of SEQ ID NO: 17 and a light chain comprising the amino acid sequence of SEQ ID NO: 22.

6. A human engineered DKK-1 antibody comprising two light chains wherein each light chain comprises the amino acid sequence of SEQ ID NO: 20, and two heavy chains wherein each heavy chain comprises the amino acid sequence of SEQ ID NO: 18.

7. A pharmaceutical composition comprising the human engineered DKK-1 antibody or antigen-binding fragment thereof of claim 1, and a pharmaceutically acceptable carrier, diluent, or excipient.

8. A method of healing bone comprising administering to a patient in need thereof an effective amount of the human engineered DKK-1 antibody or antigen-binding fragment thereof, of claim 1.

9. A method of treating cancer comprising administering to a patient in need thereof an effective amount of the human engineered DKK-1 antibody or antigen-binding fragment thereof of claim 1.

10. The method of claim 9, wherein the cancer is selected from the group consisting of multiple myeloma, breast cancer and non-small cell lung cancer.

11. A pharmaceutical composition comprising the human engineered DKK-1 antibody or antigen-binding fragment thereof of claim 6, and a pharmaceutically acceptable carrier, diluent, or excipient.

12. A method of healing bone comprising administering to a patient in need thereof an effective amount of the human engineered DKK-1 antibody or antigen-binding fragment thereof, of claim 6.

13. A method of treating cancer comprising administering to a patient in need thereof an effective amount of the human engineered DKK-1 antibody or antigen-binding fragment thereof of claim 6.

14. The method of claim 13, wherein the cancer is selected from the group consisting of multiple myeloma, breast cancer and non-small cell lung cancer.

* * * * *

UNITED STATES PATENT AND TRADEMARK OFFICE
CERTIFICATE OF CORRECTION

PATENT NO. : 8,148,498 B2
APPLICATION NO. : 12/754637
DATED : April 3, 2012
INVENTOR(S) : Marcio Chedid et al.

It is certified that error appears in the above-identified patent and that said Letters Patent is hereby corrected as shown below:

In the issued patent, please note the following corrections:

On Cover page, Item 56 Other Publications, Column 2, Line 12, delete "breat" and insert --breast--, therefor.

On Cover page, Item 56 Other Publications, Column 2, Line 15, delete "outo f" and insert --out of--, therefor.

Signed and Sealed this
Nineteenth Day of June, 2012

David J. Kappos
*Director of the United States Patent and Trademark Office*

SEQUENCE LISTING

<160> NUMBER OF SEQ ID NOS: 52

<210> SEQ ID NO 1
<211> LENGTH: 10
<212> TYPE: PRT
<213> ORGANISM: Artificial Sequence
<220> FEATURE:
<223> OTHER INFORMATION: Synthetic Construct

<400> SEQUENCE: 1

Gly Phe Thr Phe Ser Ser Tyr Thr Met Ser
1               5                   10

<210> SEQ ID NO 2
<211> LENGTH: 17
<212> TYPE: PRT
<213> ORGANISM: Artificial Sequence
<220> FEATURE:
<223> OTHER INFORMATION: Synthetic Construct

<400> SEQUENCE: 2

Thr Ile Ser Gly Gly Gly Phe Gly Thr Tyr Tyr Pro Asp Ser Val Lys
1               5                   10                  15

Gly

<210> SEQ ID NO 3
<211> LENGTH: 10
<212> TYPE: PRT
<213> ORGANISM: Artificial Sequence
<220> FEATURE:
<223> OTHER INFORMATION: Synthetic Construct

<400> SEQUENCE: 3

Pro Gly Tyr His Asn Tyr Tyr Phe Asp Ile
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Synthetic Construct

<400> SEQUENCE: 4

Pro Gly Tyr Asn Asn Tyr Tyr Phe Asp Ile
1               5                   10

```
<210> SEQ ID NO 5
<211> LENGTH: 11
<212> TYPE: PRT
<213> ORGANISM: Artificial Sequence
<220> FEATURE:
<223> OTHER INFORMATION: Synthetic Construct

<400> SEQUENCE: 5

His Ala Ser Asp Ser Ile Ser Asn Ser Leu His
1               5                   10

<210> SEQ ID NO 6
<211> LENGTH: 7
<212> TYPE: PRT
<213> ORGANISM: Artificial Sequence
<220> FEATURE:
<223> OTHER INFORMATION: Synthetic Construct

<400> SEQUENCE: 6

Tyr Gly Arg Gln Ser Ile Gln
1               5

<210> SEQ ID NO 7
<211> LENGTH: 9
<212> TYPE: PRT
<213> ORGANISM: Artificial Sequence
<220> FEATURE:
<223> OTHER INFORMATION: Synthetic Construct

<400> SEQUENCE: 7

Gln Gln Ser Glu Ser Trp Pro Leu His
1               5

<210> SEQ ID NO 8
<211> LENGTH: 7
<212> TYPE: PRT
<213> ORGANISM: Artificial Sequence
<220> FEATURE:
<223> OTHER INFORMATION: Synthetic Construct

<400> SEQUENCE: 8

Tyr Ala Arg Gln Ser Ile Gln
1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic Construct

<400> SEQUENCE: 9

Gln Gln Ser Ala Ser Trp Pro Leu His
1               5

<210> SEQ ID NO 10
<211> LENGTH: 7
<212> TYPE: PRT
<213> ORGANISM: Artificial Sequence
<220> FEATURE:
<223> OTHER INFORMATION: Synthetic Construct

<400> SEQUENCE: 10

Tyr Ala Arg Gln Ser Glu Gln
1               5

<210> SEQ ID NO 11
```

```
<211> LENGTH: 119
<212> TYPE: PRT
<213> ORGANISM: Artificial Sequence
<220> FEATURE:
<223> OTHER INFORMATION: Synthetic Construct

<400> SEQUENCE: 11

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Thr Met Ser Trp Val Arg Gln Ala Pro Gly Lys Gly Leu Glu Trp Val
        35                  40                  45

Ala Thr Ile Ser Gly Gly Gly Phe Gly Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Pro Gly Tyr His Asn Tyr Tyr Phe Asp Ile Trp Gly Gln Gly
            100                 105                 110

Thr Thr Val Thr Val Ser Ser
        115

<210> SEQ ID NO 12
<211> LENGTH: 119
<212> TYPE: PRT
<213> ORGANISM: Artificial Sequence
<220> FEATURE:
<223> OTHER INFORMATION: Synthetic Construct

<400> SEQUENCE: 12

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Thr Met Ser Trp Val Arg Gln Ala Pro Gly Lys Gly Leu Glu Trp Val
        35                  40                  45

Ala Thr Ile Ser Gly Gly Gly Phe Gly Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Pro Gly Tyr Asn Asn Tyr Tyr Phe Asp Ile Trp Gly Gln Gly
            100                 105                 110

Thr Thr Val Thr Val Ser Ser
        115

<210> SEQ ID NO 13
<211> LENGTH: 107
<212> TYPE: PRT
<213> ORGANISM: Artificial Sequence
<220> FEATURE:
<223> OTHER INFORMATION: Synthetic Construct

<400> SEQUENCE: 13

Glu Ile Val Leu Thr Gln Ser Pro Ala Thr Leu Ser Leu Ser Pro Gly
1               5                   10                  15

Glu Arg Ala Thr Leu Ser Cys His Ala Ser Asp Ser Ile Ser Asn Ser
```

```
                    20                  25                  30

Leu His Trp Tyr Gln Gln Lys Pro Gly Gln Ala Pro Arg Leu Leu Ile
            35                  40                  45

Tyr Tyr Gly Arg Gln Ser Ile Gln Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Glu Ser Trp Pro Leu
                85                  90                  95

His Phe Gly Gly Gly Thr Lys Val Glu Ile Lys
            100                 105

<210> SEQ ID NO 14
<211> LENGTH: 107
<212> TYPE: PRT
<213> ORGANISM: Artificial Sequence
<220> FEATURE:
<223> OTHER INFORMATION: Synthetic Construct

<400> SEQUENCE: 14

Glu Ile Val Leu Thr Gln Ser Pro Ala Thr Leu Ser Leu Ser Pro Gly
1               5                   10                  15

Glu Arg Ala Thr Leu Ser Cys His Ala Ser Asp Ser Ile Ser Asn Ser
                20                  25                  30

Leu His Trp Tyr Gln Gln Lys Pro Gly Gln Ala Pro Arg Leu Leu Ile
            35                  40                  45

Tyr Tyr Ala Arg Gln Ser Ile Gln Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Glu Ser Trp Pro Leu
                85                  90                  95

His Phe Gly Gly Gly Thr Lys Val Glu Ile Lys
            100                 105

<210> SEQ ID NO 15
<211> LENGTH: 107
<212> TYPE: PRT
<213> ORGANISM: Artificial Sequence
<220> FEATURE:
<223> OTHER INFORMATION: Synthetic Construct

<400> SEQUENCE: 15

Glu Ile Val Leu Thr Gln Ser Pro Ala Thr Leu Ser Leu Ser Pro Gly
1               5                   10                  15

Glu Arg Ala Thr Leu Ser Cys His Ala Ser Asp Ser Ile Ser Asn Ser
                20                  25                  30

Leu His Trp Tyr Gln Gln Lys Pro Gly Gln Ala Pro Arg Leu Leu Ile
            35                  40                  45

Tyr Tyr Gly Arg Gln Ser Ile Gln Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ala Ser Trp Pro Leu
                85                  90                  95

His Phe Gly Gly Gly Thr Lys Val Glu Ile Lys
            100                 105
```

<210> SEQ ID NO 16
<211> LENGTH: 107
<212> TYPE: PRT
<213> ORGANISM: Artificial Sequence
<220> FEATURE:
<223> OTHER INFORMATION: Synthetic Construct

<400> SEQUENCE: 16

```
Glu Ile Val Leu Thr Gln Ser Pro Ala Thr Leu Ser Leu Ser Pro Gly
1               5                   10                  15

Glu Arg Ala Thr Leu Ser Cys His Ala Ser Asp Ser Ile Ser Asn Ser
            20                  25                  30

Leu His Trp Tyr Gln Gln Lys Pro Gly Gln Ala Pro Arg Leu Leu Ile
        35                  40                  45

Tyr Tyr Ala Arg Gln Ser Glu Gln Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ala Ser Trp Pro Leu
                85                  90                  95

His Phe Gly Gly Gly Thr Lys Val Glu Ile Lys
            100                 105
```

<210> SEQ ID NO 17
<211> LENGTH: 445
<212> TYPE: PRT
<213> ORGANISM: Artificial Sequence
<220> FEATURE:
<223> OTHER INFORMATION: Synthetic Construct

<400> SEQUENCE: 17

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Thr Met Ser Trp Val Arg Gln Ala Pro Gly Lys Gly Leu Glu Trp Val
        35                  40                  45

Ala Thr Ile Ser Gly Gly Gly Phe Gly Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Pro Gly Tyr His Asn Tyr Tyr Phe Asp Ile Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
```

```
            210                 215                 220
Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
                260                 265                 270

Gln Phe Asn Trp Tyr Val Asp Gly Val Glu Val His Asn Ala Lys Thr
            275                 280                 285

Lys Pro Arg Glu Glu Gln Phe Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Gln Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly
                435                 440                 445

<210> SEQ ID NO 18
<211> LENGTH: 445
<212> TYPE: PRT
<213> ORGANISM: Artificial Sequence
<220> FEATURE:
<223> OTHER INFORMATION: Synthetic Construct

<400> SEQUENCE: 18

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Thr Met Ser Trp Val Arg Gln Ala Pro Gly Lys Gly Leu Glu Trp Val
            35                  40                  45

Ala Thr Ile Ser Gly Gly Gly Phe Gly Thr Tyr Tyr Pro Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Pro Gly Tyr Asn Asn Tyr Tyr Phe Asp Ile Trp Gly Gln Gly
                100                 105                 110

Thr Thr Val Thr Val Ser Ser Ala Ser Thr Lys Gly Pro Ser Val Phe
            115                 120                 125

Pro Leu Ala Pro Cys Ser Arg Ser Thr Ser Glu Ser Thr Ala Ala Leu
130                 135                 140
```

```
Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
        180                 185                 190

Ser Ser Leu Gly Thr Lys Thr Tyr Thr Cys Asn Val Asp His Lys Pro
    195                 200                 205

Ser Asn Thr Lys Val Asp Lys Arg Val Glu Ser Lys Tyr Gly Pro Pro
210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Gly
        435                 440                 445

<210> SEQ ID NO 19
<211> LENGTH: 214
<212> TYPE: PRT
<213> ORGANISM: Artificial Sequence
<220> FEATURE:
<223> OTHER INFORMATION: Synthetic Construct

<400> SEQUENCE: 19

Glu Ile Val Leu Thr Gln Ser Pro Ala Thr Leu Ser Leu Ser Pro Gly
1               5                   10                  15

Glu Arg Ala Thr Leu Ser Cys His Ala Ser Asp Ser Ile Ser Asn Ser
            20                  25                  30

Leu His Trp Tyr Gln Gln Lys Pro Gly Gln Ala Pro Arg Leu Leu Ile
        35                  40                  45

Tyr Tyr Gly Arg Gln Ser Ile Gln Gly Ile Pro Ala Arg Phe Ser Gly
    50                  55                  60
```

```
Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Ser Glu Ser Trp Pro Leu
                 85                  90                  95

His Phe Gly Gly Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 20
<211> LENGTH: 214
<212> TYPE: PRT
<213> ORGANISM: Artificial Sequence
<220> FEATURE:
<223> OTHER INFORMATION: Synthetic Construct

<400> SEQUENCE: 20

Glu Ile Val Leu Thr Gln Ser Pro Ala Thr Leu Ser Leu Ser Pro Gly
  1               5                  10                  15

Glu Arg Ala Thr Leu Ser Cys His Ala Ser Asp Ser Ile Ser Asn Ser
                 20                  25                  30

Leu His Trp Tyr Gln Gln Lys Pro Gly Gln Ala Pro Arg Leu Leu Ile
             35                  40                  45

Tyr Tyr Ala Arg Gln Ser Ile Gln Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Ser Glu Ser Trp Pro Leu
                 85                  90                  95

His Phe Gly Gly Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
```

<210> SEQ ID NO 21
<211> LENGTH: 214
<212> TYPE: PRT
<213> ORGANISM: Artificial Sequence
<220> FEATURE:
<223> OTHER INFORMATION: Synthetic Construct

<400> SEQUENCE: 21

```
Glu Ile Val Leu Thr Gln Ser Pro Ala Thr Leu Ser Leu Ser Pro Gly
1               5                   10                  15

Glu Arg Ala Thr Leu Ser Cys His Ala Ser Asp Ser Ile Ser Asn Ser
            20                  25                  30

Leu His Trp Tyr Gln Gln Lys Pro Gly Gln Ala Pro Arg Leu Leu Ile
        35                  40                  45

Tyr Tyr Gly Arg Gln Ser Ile Gln Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ala Ser Trp Pro Leu
                85                  90                  95

His Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 22
<211> LENGTH: 214
<212> TYPE: PRT
<213> ORGANISM: Artificial Sequence
<220> FEATURE:
<223> OTHER INFORMATION: Synthetic Construct

<400> SEQUENCE: 22

```
Glu Ile Val Leu Thr Gln Ser Pro Ala Thr Leu Ser Leu Ser Pro Gly
1               5                   10                  15

Glu Arg Ala Thr Leu Ser Cys His Ala Ser Asp Ser Ile Ser Asn Ser
            20                  25                  30

Leu His Trp Tyr Gln Gln Lys Pro Gly Gln Ala Pro Arg Leu Leu Ile
        35                  40                  45

Tyr Tyr Ala Arg Gln Ser Glu Gln Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ala Ser Trp Pro Leu
```

```
                       85                  90                  95
His Phe Gly Gly Gly Thr Lys Val Glu Ile Lys Arg Thr Val Ala Ala
                    100                 105                 110

Pro Ser Val Phe Ile Phe Pro Pro Ser Asp Glu Gln Leu Lys Ser Gly
                    115                 120                 125

Thr Ala Ser Val Val Cys Leu Leu Asn Asn Phe Tyr Pro Arg Glu Ala
                    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                    165                 170                 175

Ser Thr Leu Thr Leu Ser Lys Ala Asp Tyr Glu Lys His Lys Val Tyr
                    180                 185                 190

Ala Cys Glu Val Thr His Gln Gly Leu Ser Ser Pro Val Thr Lys Ser
                    195                 200                 205

Phe Asn Arg Gly Glu Cys
    210
```

<210> SEQ ID NO 23
<211> LENGTH: 1335
<212> TYPE: DNA
<213> ORGANISM: Artificial Sequence
<220> FEATURE:
<223> OTHER INFORMATION: Synthetic Construct

<400> SEQUENCE: 23

```
gaggtgcagc tggtggagtc tgggggaggc ttggtccagc ctggggggtc cctgagactc      60
tcctgtgcag cctctggatt cactttcagt agctatacca tgtcttgggt ccgccaggct     120
ccagggaagg ggctggagtg ggtggccacc atttccggtg gtggtttcgg cacatactat     180
cccgacagtg tgaagggtcg attcaccatc tccagagaca acgccaagaa ctcactgtat     240
ctgcaaatga acagcctgag agccgaggac acggctgtgt attactgtgc agagacctgga     300
tatcacaact actactttga catctggggc caagggacca cggtcaccgt ctcctcagcc     360
tccaccaagg gcccatcggt cttccccgcta gcgccctgct ccaggagcac ctccgagagc     420
acagccgccc tgggctgcct ggtcaaggac tacttccccg aaccggtgac ggtgtcgtgg     480
aactcaggcg ccctgaccag cggcgtgcac accttcccgg ctgtcctaca gtcctcagga     540
ctctactccc tcagcagcgt ggtgaccgtg ccctccagca gcttgggcac gaagacctac     600
acctgcaacg tagatcacaa gcccagcaac accaaggtgg acaagagagt tgagtccaaa     660
tatggtcccc catgcccacc ctgcccagca cctgaggccg ccggggggacc atcagtcttc     720
ctgttccccc caaaacccaa ggacactctc atgatctccc ggacccctga ggtcacgtgc     780
gtggtggtgg acgtgagcca ggaagacccc gaggtccagt tcaactggta cgtggatggc     840
gtggaggtgc ataatgccaa gacaaagccg cgggaggagc agttcaacag cacgtaccgt     900
gtggtcagcg tcctcaccgt cctgcaccag gactggctga acggcaagga gtacaagtgc     960
aaggtctcca acaaaggcct cccgtcctcc atcgagaaaa ccatctccaa agccaaaggg    1020
cagccccgag agccacaggt gtacaccctg cccccatccc aggaggagat gaccaagaac    1080
caggtcagcc tgacctgcct ggtcaaaggc ttctacccca gcgacatcgc cgtggagtgg    1140
gaaagcaatg ggcagccgga gaacaactac aagaccacgc ctcccgtgct ggactccgac    1200
ggctccttct tcctctacag caggctaacc gtggacaaga gcaggtggca ggaggggaat    1260
gtcttctcat gctccgtgat gcatgaggct ctgcacaacc actacacaca gaagagcctc    1320
```
tccctgtctc tgggt                                                      1335

<210> SEQ ID NO 24
<211> LENGTH: 1335
<212> TYPE: DNA
<213> ORGANISM: Artificial Sequence
<220> FEATURE:
<223> OTHER INFORMATION: Synthetic Construct

<400> SEQUENCE: 24
gaggtgcagc tggtggagtc tggggggaggc ttggtccagc ctggggggtc cctgagactc      60
tcctgtgcag cctctggatt cactttcagt agctatacca tgtcttgggt ccgccaggct     120
ccagggaagg ggctggagtg ggtggccacc atttccggtg gtggtttcgg cacatactat     180
cccgacagtg tgaagggtcg attcaccatc tccagagaca cgccaagaa ctcactgtat      240 ctgcaaatga acagcctgag agccgaggac acggctgtgt attactgtgc gagacctgga     300
tataataact actactttga catctggggc caagggacca cggtcaccgt ctcctcagcc     360
tccaccaagg gcccatcggt cttccccgcta cgccctgct ccaggagcac ctccgagagc     420
acagccgccc tgggctgcct ggtcaaggac tacttcccg aaccggtgac ggtgtcgtgg     480
aactcaggcg ccctgaccag cggcgtgcac accttcccgg ctgtcctaca gtcctcagga     540
ctctactccc tcagcagcgt ggtgaccgtg ccctccagca gcttgggcac gaagacctac     600
acctgcaacg tagatcacaa gcccagcaac accaaggtgg acaagagagt tgagtccaaa     660
tatggtcccc catgcccacc ctgcccagca cctgaggccg ccggggggacc atcagtcttc     720 ctgttccccc caaaacccaa ggacactctc atgatctccc ggacccctga ggtcacgtgc     780
gtggtggtgg acgtgagcca ggaagacccc gaggtccagt tcaactggta cgtggatggc     840
gtggaggtgc ataatgccaa gacaaagccg cgggaggagc agttcaacag cacgtaccgt     900
gtggtcagcg tcctcaccgt cctgcaccag gactggctga acggcaagga gtacaagtgc     960
aaggtctcca acaaaggcct cccgtcctcc atcgagaaaa ccatctccaa agccaaaggg    1020
cagccccgag agccacaggt gtacaccctg cccccatccc aggaggagat gaccaagaac    1080
caggtcagcc tgacctgcct ggtcaaaggc ttctacccca gcgacatcgc cgtggagtgg    1140
gaaagcaatg ggcagccgga gaacaactac aagaccacgc ctcccgtgct ggactccgac    1200
ggctccttct cctctacag caggctaacc gtggacaaga gcaggtggca ggaggggaat    1260
gtcttctcat gctccgtgat gcatgaggct ctgcacaacc actacacaca gaagagcctc    1320
tccctgtctc tgggt                                                      1335

<210> SEQ ID NO 25
<211> LENGTH: 642
<212> TYPE: DNA
<213> ORGANISM: Artificial Sequence
<220> FEATURE:
<223> OTHER INFORMATION: Synthetic Construct

<400> SEQUENCE: 25
gaaattgtgt tgacacagtc tccagccacc ctgtctttgt ctccagggga aagagccacc      60
ctctcctgcc acgccagcga cagtattagc aacagcctac actggtacca acagaaacct     120
ggccaggctc ccaggctcct catctattat ggcagacagt ccatccaggg catcccagcc     180
aggttcagtg gcagtgggtc tgggacagac ttcactctca ccatcagcag cctagagcct     240
gaagattttg cagtttatta ctgtcaacag agtgagagct ggccgctcca cttcggcgga     300
gggaccaagg tggagatcaa acgaactgtg gctgcaccat ctgtcttcat cttcccgcca     360

-continued

```
tctgatgagc agttgaaatc tggaactgcc tctgttgtgt gcctgctgaa taacttctat      420
cccagagagg ccaaagtaca gtggaaggtg gataacgccc tccaatcggg taactcccag      480
gagagtgtca cagagcagga cagcaaggac agcacctaca gcctcagcag caccctgacg      540
ctgagcaaag cagactacga gaaacacaaa gtctacgcct gcgaagtcac ccatcagggc      600
ctgagctcgc ccgtcacaaa gagcttcaac aggggagagt gc                        642
```

<210> SEQ ID NO 26
<211> LENGTH: 642
<212> TYPE: DNA
<213> ORGANISM: Artificial Sequence
<220> FEATURE:
<223> OTHER INFORMATION: Synthetic Construct

<400> SEQUENCE: 26

```
gaaattgtgt tgacacagtc tccagccacc ctgtctttgt ctccagggga aagagccacc       60
ctctcctgcc acgccagcga cagtattagc aacagcctac actggtacca acagaaacct      120
ggccaggctc ccaggctcct catctattat gctagacagt ccatccaggg catcccagcc      180
aggttcagtg gcagtgggtc tgggacagac ttcactctca ccatcagcag cctagagcct      240
gaagattttg cagtttatta ctgtcaacag agtgagagct ggccgctcca cttcggcgga      300
gggaccaagg tggagatcaa acgaactgtg gctgcaccat ctgtcttcat cttcccgcca      360
tctgatgagc agttgaaatc tggaactgcc tctgttgtgt gcctgctgaa taacttctat      420
cccagagagg ccaaagtaca gtggaaggtg gataacgccc tccaatcggg taactcccag      480
gagagtgtca cagagcagga cagcaaggac agcacctaca gcctcagcag caccctgacg      540
ctgagcaaag cagactacga gaaacacaaa gtctacgcct gcgaagtcac ccatcagggc      600
ctgagctcgc ccgtcacaaa gagcttcaac aggggagagt gc                        642
```

<210> SEQ ID NO 27
<211> LENGTH: 642
<212> TYPE: DNA
<213> ORGANISM: Artificial Sequence
<220> FEATURE:
<223> OTHER INFORMATION: Synthetic Construct

<400> SEQUENCE: 27

```
gaaattgtgt tgacacagtc tccagccacc ctgtctttgt ctccagggga aagagccacc       60
ctctcctgcc acgccagcga cagtattagc aacagcctac actggtacca acagaaacct      120
ggccaggctc ccaggctcct catctattat ggcagacagt ccatccaggg catcccagcc      180
aggttcagtg gcagtgggtc tgggacagac ttcactctca ccatcagcag cctagagcct      240
gaagattttg cagtttatta ctgtcaacag agtgccagct ggccgctcca cttcggcgga      300
gggaccaagg tggagatcaa acgaactgtg gctgcaccat ctgtcttcat cttcccgcca      360
tctgatgagc agttgaaatc tggaactgcc tctgttgtgt gcctgctgaa taacttctat      420
cccagagagg ccaaagtaca gtggaaggtg gataacgccc tccaatcggg taactcccag      480
gagagtgtca cagagcagga cagcaaggac agcacctaca gcctcagcag caccctgacg      540
ctgagcaaag cagactacga gaaacacaaa gtctacgcct gcgaagtcac ccatcagggc      600
ctgagctcgc ccgtcacaaa gagcttcaac aggggagagt gc                        642
```

<210> SEQ ID NO 28
<211> LENGTH: 642
<212> TYPE: DNA
<213> ORGANISM: Artificial Sequence
<220> FEATURE:

<223> OTHER INFORMATION: Synthetic Construct

<400> SEQUENCE: 28

```
gaaattgtgt tgacacagtc tccagccacc ctgtctttgt ctccagggga aagagccacc    60
ctctcctgcc acgccagcga cagtattagc aacagcctac actggtacca acagaaacct   120
ggccaggctc ccaggctcct catctattat gctagacagt ccgagcaggg catcccagcc   180
aggttcagtg gcagtgggtc tgggacagac ttcactctca ccatcagcag cctagagcct   240
gaagattttg cagtttatta ctgtcaacag agtgccagct ggccgctcca cttcggcgga   300
gggaccaagg tggagatcaa acgaactgtg gctgcaccat ctgtcttcat cttcccgcca   360
tctgatgagc agttgaaatc tggaactgcc tctgttgtgt gcctgctgaa taacttctat   420
cccagagagg ccaaagtaca gtggaaggtg gataacgccc tccaatcggg taactcccag   480
gagagtgtca cagagcagga cagcaaggac agcacctaca gcctcagcag caccctgacg   540
ctgagcaaag cagactacga gaaacacaaa gtctacgcct gcgaagtcac ccatcagggc   600
ctgagctcgc ccgtcacaaa gagcttcaac aggggagagt gc                      642
```

<210> SEQ ID NO 29
<211> LENGTH: 235
<212> TYPE: PRT
<213> ORGANISM: Homo sapiens

<400> SEQUENCE: 29

```
Thr Leu Asn Ser Val Leu Asn Ser Asn Ala Ile Lys Asn Leu Pro Pro
1               5                   10                  15

Pro Leu Gly Gly Ala Ala Gly His Pro Gly Ser Ala Val Ser Ala Ala
            20                  25                  30

Pro Gly Ile Leu Tyr Pro Gly Gly Asn Lys Tyr Gln Thr Ile Asp Asn
        35                  40                  45

Tyr Gln Pro Tyr Pro Cys Ala Glu Asp Glu Cys Gly Thr Asp Glu
    50                  55                  60

Tyr Cys Ala Ser Pro Thr Arg Gly Gly Asp Ala Gly Val Gln Ile Cys
65                  70                  75                  80

Leu Ala Cys Arg Lys Arg Arg Lys Arg Cys Met Arg His Ala Met Cys
                85                  90                  95

Cys Pro Gly Asn Tyr Cys Lys Asn Gly Ile Cys Val Ser Ser Asp Gln
            100                 105                 110

Asn His Phe Arg Gly Glu Ile Glu Thr Ile Thr Glu Ser Phe Gly
        115                 120                 125

Asn Asp His Ser Thr Leu Asp Gly Tyr Ser Arg Arg Thr Thr Leu Ser
    130                 135                 140

Ser Lys Met Tyr His Thr Lys Gly Gln Glu Gly Ser Val Cys Leu Arg
145                 150                 155                 160

Ser Ser Asp Cys Ala Ser Gly Leu Cys Cys Ala Arg His Phe Trp Ser
                165                 170                 175

Lys Ile Cys Lys Pro Val Leu Lys Glu Gly Gln Val Cys Thr Lys His
            180                 185                 190

Arg Arg Lys Gly Ser His Gly Leu Glu Ile Phe Gln Arg Cys Tyr Cys
        195                 200                 205

Gly Glu Gly Leu Ser Cys Arg Ile Gln Lys Asp His His Gln Ala Ser
    210                 215                 220

Asn Ser Ser Arg Leu His Thr Cys Gln Arg His
225                 230                 235
```

```
<210> SEQ ID NO 30
<211> LENGTH: 234
<212> TYPE: PRT
<213> ORGANISM: Cebus albifrons

<400> SEQUENCE: 30

Thr Leu Asn Ser Val Leu Asn Ser Asn Ala Ile Lys Asn Leu Pro Pro
 1               5                  10                  15

Pro Leu Gly Gly Ala Ala Gly His Pro Gly Ser Ala Val Ser Ala Ala
             20                  25                  30

Pro Gly Ile Leu Tyr Pro Gly Gly Asn Lys Tyr Gln Thr Ile Asp Asn
         35                  40                  45

Tyr Gln Pro Tyr Pro Cys Ala Glu Asp Glu Glu Cys Gly Thr Asp Glu
 50                  55                  60

Tyr Cys Ala Ser Pro Thr Arg Gly Gly Asp Ala Gly Val Gln Ile Cys
 65                  70                  75                  80

Leu Ala Cys Arg Lys Arg Arg Lys Arg Cys Met Arg His Ala Met Cys
                 85                  90                  95

Cys Pro Gly Asn Tyr Cys Lys Asn Gly Ile Cys Val Ser Ser Asp Gln
            100                 105                 110

Asn Asn Phe Arg Gly Glu Ile Glu Glu Thr Ile Thr Glu Ser Phe Gly
        115                 120                 125

Asn Asp His Ser Thr Leu Asp Gly Tyr Ser Arg Thr Thr Leu Ser
130                 135                 140

Ser Lys Met Tyr His Ser Lys Gly Gln Glu Gly Ser Val Cys Leu Arg
145                 150                 155                 160

Ser Ser Asp Cys Ala Thr Gly Leu Cys Cys Ala Arg His Phe Trp Ser
                165                 170                 175

Lys Ile Cys Lys Pro Val Leu Lys Glu Gly Gln Val Cys Thr Lys His
            180                 185                 190

Arg Arg Lys Gly Ser His Gly Leu Glu Ile Phe Gln Arg Cys Tyr Cys
        195                 200                 205

Gly Glu Gly Leu Ser Cys Arg Ile Gly Lys Asp His His Gln Ala Ser
    210                 215                 220

Asn Ser Ser Arg Leu His Thr Cys Gln Arg
225                 230

<210> SEQ ID NO 31
<211> LENGTH: 252
<212> TYPE: PRT
<213> ORGANISM: Rattus rattus

<400> SEQUENCE: 31

Thr Leu Asn Ser Val Leu Ile Asn Ser Asn Ala Ile Lys Asn Leu Pro
 1               5                  10                  15

Pro Pro Leu Gly Gly Ala Gly Gly Gln Pro Gly Ser Ala Val Ser Val
             20                  25                  30

Ala Pro Gly Val Leu Tyr Glu Gly Gly Asn Lys Tyr Gln Thr Leu Asp
         35                  40                  45

Asn Tyr Gln Pro Tyr Pro Cys Ala Glu Asp Glu Glu Cys Gly Thr Asp
 50                  55                  60

Glu Tyr Cys Ser Ser Pro Ser Arg Gly Ala Ala Gly Val Gly Gly Val
 65                  70                  75                  80

Gln Ile Cys Leu Ala Cys Arg Lys Arg Arg Lys Arg Cys Met Arg His
                 85                  90                  95

Ala Met Cys Cys Pro Gly Asn Tyr Cys Lys Asn Gly Ile Cys Met Pro
            100                 105                 110
```

```
Ser Asp His Ser His Leu Pro Arg Gly Glu Ile Glu Glu Gly Ile Ile
            115                 120                 125

Glu Asn Leu Gly Asn Asp His Gly Ala Gly Asp Gly Tyr Pro Arg Arg
        130                 135                 140

Thr Thr Leu Thr Ser Lys Ile Tyr His Thr Lys Gly Gln Glu Gly Ser
145                 150                 155                 160

Val Cys Leu Arg Ser Ser Asp Cys Ala Thr Gly Leu Cys Cys Ala Arg
                165                 170                 175

His Phe Trp Ser Lys Ile Cys Lys Pro Val Leu Lys Glu Gly Gln Val
            180                 185                 190

Cys Thr Lys His Arg Arg Lys Gly Ser His Gly Leu Glu Ile Phe Gln
        195                 200                 205

Arg Cys Tyr Cys Gly Glu Gly Leu Ala Cys Arg Ile Gln Lys Asp His
    210                 215                 220

His Gln Thr Ser Asn Ser Ser Arg Leu His Thr Cys Gln Arg His Ala
225                 230                 235                 240

Phe Ile Asp Tyr Lys Asp Asp Asp Lys His Val
                245                 250

<210> SEQ ID NO 32
<211> LENGTH: 236
<212> TYPE: PRT
<213> ORGANISM: Lepus americanus

<400> SEQUENCE: 32

Thr Leu Asn Ser Val Leu Val Asn Ser Asn Ala Ile Lys Asn Leu Pro
1               5                   10                  15

Pro Pro Leu Gly Gly Ala Asn Gly His Pro Gly Ser Ala Val Ser Ala
            20                  25                  30

Thr Pro Gly Ile Leu Tyr Glu Gly Gly Asn Lys Tyr Leu Pro Leu Asp
        35                  40                  45

Asn Tyr Gln Pro Tyr Pro Cys Thr Glu Asp Glu Cys Gly Thr Asp
    50                  55                  60

Glu Tyr Cys Ala Ser Pro Ala Arg Gly Gly Ala Gly Val Gln Ile
65                  70                  75                  80

Cys Leu Ala Cys Arg Lys Arg Arg Lys Arg Cys Met Arg His Ala Met
                85                  90                  95

Cys Cys Pro Gly Asn Tyr Cys Lys Asn Gly Ile Cys Met Pro Ser Asp
            100                 105                 110

His Asn His Phe His Arg Gly Glu Ile Glu Glu Thr Ile Val Glu Ser
        115                 120                 125

Phe Gly Asn Asp His Ser Thr Ser Asp Gly Tyr Ser Arg Arg Thr Thr
    130                 135                 140

Leu Ser Ser Lys Met Tyr His Ala Lys Gly Gln Glu Gly Ser Val Cys
145                 150                 155                 160

Leu Arg Ser Ser Asp Cys Ala Thr Gly Leu Cys Cys Ala Arg His Phe
                165                 170                 175

Trp Ser Lys Ile Cys Lys Pro Val Leu Lys Glu Gly Gln Val Cys Thr
            180                 185                 190

Lys His Arg Arg Lys Gly Ser His Gly Leu Glu Ile Phe Gln Arg Cys
        195                 200                 205

Tyr Cys Gly Asp Gly Leu Ser Cys Arg Leu Gln Asn Asp Gln His Glu
    210                 215                 220

Ala Ser Asn Ser Ser Arg Leu His Thr Cys Gln Arg
225                 230                 235
```

<210> SEQ ID NO 33
<211> LENGTH: 241
<212> TYPE: PRT
<213> ORGANISM: Mus musculus

<400> SEQUENCE: 33

Thr Leu Asn Ser Val Leu Ile Asn Ser Asn Ala Ile Lys Asn Leu Pro
1               5                   10                  15

Pro Pro Leu Gly Gly Ala Gly Gly Gln Pro Gly Ser Ala Val Ser Val
            20                  25                  30

Ala Pro Gly Val Leu Tyr Glu Gly Asn Lys Tyr Gln Thr Leu Asp
        35                  40                  45

Asn Tyr Gln Pro Tyr Pro Cys Ala Glu Asp Glu Glu Cys Gly Ser Asp
50                  55                  60

Glu Tyr Cys Ser Ser Pro Ser Arg Gly Ala Ala Gly Val Gly Gly Val
65                  70                  75                  80

Gln Ile Cys Leu Ala Cys Arg Lys Arg Lys Arg Cys Met Thr His
                85                  90                  95

Ala Met Cys Cys Pro Gly Asn Tyr Cys Lys Asn Gly Ile Cys Met Pro
            100                 105                 110

Ser Asp His Ser His Phe Pro Arg Gly Glu Ile Glu Glu Ser Ile Ile
            115                 120                 125

Glu Asn Leu Gly Asn Asp His Asn Ala Ala Gly Asp Gly Tyr Pro
130                 135                 140

Arg Arg Thr Thr Leu Thr Ser Lys Ile Tyr His Thr Lys Gly Gln Glu
145                 150                 155                 160

Gly Ser Val Cys Leu Arg Ser Ser Asp Cys Ala Ala Gly Leu Cys Cys
                165                 170                 175

Ala Arg His Phe Trp Ser Lys Ile Cys Lys Pro Val Leu Lys Glu Gly
            180                 185                 190

Gln Val Cys Thr Lys His Lys Arg Lys Gly Ser His Gly Leu Glu Ile
            195                 200                 205

Phe Gln Arg Cys Tyr Cys Gly Glu Gly Leu Ala Cys Arg Ile Gln Lys
    210                 215                 220

Asp His His Gln Ala Ser Asn Ser Ser Arg Leu His Thr Cys Gln Arg
225                 230                 235                 240

His

<210> SEQ ID NO 34
<211> LENGTH: 214
<212> TYPE: PRT
<213> ORGANISM: Artificial Sequence
<220> FEATURE:
<223> OTHER INFORMATION: Synthetic Construct

<400> SEQUENCE: 34

Asp Ile Leu Leu Thr Gln Ser Pro Ala Thr Leu Ser Val Thr Pro Gly
1               5                   10                  15

Asp Ser Val Ser Leu Ser Cys Arg Ala Ser Asp Ser Ile Ser Gly Ser
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Thr Asp Phe Thr Leu Ser Ile Asn Ser Val Glu Thr
65                  70                  75                  80

Glu Asp Phe Gly Met Tyr Phe Cys Gln Gln Ser Asn Ser Trp Pro Leu
                    85                  90                  95

Asn Phe Gly Ala Gly Thr Lys Leu Glu Leu Lys Arg Ala Asp Ala Ala
                100                 105                 110

Pro Thr Val Ser Ile Phe Pro Pro Ser Thr Glu Gln Leu Ala Thr Gly
                115                 120                 125

Gly Ala Ser Val Val Cys Leu Met Asn Asn Phe Tyr Pro Arg Asp Ile
        130                 135                 140

Ser Val Lys Trp Lys Ile Asp Gly Thr Glu Arg Arg Asp Gly Val Leu
145                 150                 155                 160

Asp Ser Val Thr Asp Gln Asp Ser Lys Asp Ser Thr Tyr Ser Met Ser
                165                 170                 175

Ser Thr Leu Ser Leu Ser Lys Ala Asp Tyr Glu Ser His Asn Leu Tyr
                180                 185                 190

Thr Cys Glu Val Val His Lys Thr Ser Ser Ser Pro Val Val Lys Ser
                195                 200                 205

Phe Asn Arg Asn Glu Cys
        210

<210> SEQ ID NO 35
<211> LENGTH: 445
<212> TYPE: PRT
<213> ORGANISM: Artificial Sequence
<220> FEATURE:
<223> OTHER INFORMATION: Synthetic Construct

<400> SEQUENCE: 35

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
                20                  25                  30

Thr Met Ser Trp Val Arg Gln Thr Pro Glu Lys Arg Leu Glu Trp Val
            35                  40                  45

Ala Thr Ile Ser Gly Gly Gly Asn Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Leu Ser Ser Leu Arg Ser Glu Asp Thr Ala Leu Tyr Tyr Cys
                85                  90                  95

Ala Arg Pro Gly Tyr Asn Asn Tyr Tyr Phe Asp Tyr Trp Gly Gln Gly
                100                 105                 110

Thr Thr Leu Thr Val Ser Ser Ala Lys Thr Thr Pro Pro Ser Val Tyr
            115                 120                 125

Pro Leu Ala Pro Gly Thr Ala Leu Lys Ser Asn Ser Met Val Thr Leu
        130                 135                 140

Gly Cys Leu Val Lys Gly Tyr Phe Pro Glu Pro Val Thr Val Thr Trp
145                 150                 155                 160

Asn Ser Gly Ala Leu Ser Ser Gly Val His Thr Phe Pro Ala Val Leu
                165                 170                 175

Gln Ser Gly Leu Tyr Thr Leu Thr Ser Ser Val Thr Val Pro Ser Ser
                180                 185                 190

Thr Trp Pro Ser Gln Thr Val Thr Cys Asn Val Ala His Pro Ala Ser
            195                 200                 205

Ser Thr Lys Val Asp Lys Lys Ile Val Pro Arg Asn Cys Gly Gly Asp
        210                 215                 220

```
Cys Lys Pro Cys Ile Cys Thr Gly Ser Glu Val Ser Ser Val Phe Ile
225                 230                 235                 240

Phe Pro Pro Lys Pro Lys Asp Val Leu Thr Ile Thr Leu Thr Pro Lys
                245                 250                 255

Val Thr Cys Val Val Val Asp Ile Ser Gln Asp Asp Pro Glu Val His
            260                 265                 270

Phe Ser Trp Phe Val Asp Asp Val Glu Val His Thr Ala Gln Thr Arg
        275                 280                 285

Pro Pro Glu Glu Gln Phe Asn Ser Thr Phe Arg Ser Val Ser Glu Leu
    290                 295                 300

Pro Ile Leu His Gln Asp Trp Leu Asn Gly Arg Thr Phe Arg Cys Lys
305                 310                 315                 320

Val Thr Ser Ala Ala Phe Pro Ser Pro Ile Glu Lys Thr Ile Ser Lys
                325                 330                 335

Pro Glu Gly Arg Thr Gln Val Pro His Val Tyr Thr Met Ser Pro Thr
            340                 345                 350

Lys Glu Glu Met Thr Gln Asn Glu Val Ser Ile Thr Cys Met Val Lys
        355                 360                 365

Gly Phe Tyr Pro Pro Asp Ile Tyr Val Glu Trp Gln Met Asn Gly Gln
    370                 375                 380

Pro Gln Glu Asn Tyr Lys Asn Thr Pro Pro Thr Met Asp Thr Asp Gly
385                 390                 395                 400

Ser Tyr Phe Leu Tyr Ser Lys Leu Asn Val Lys Lys Glu Lys Trp Gln
                405                 410                 415

Gln Gly Asn Thr Phe Thr Cys Ser Val Leu His Glu Gly Leu His Asn
            420                 425                 430

His His Thr Glu Lys Ser Leu Ser His Ser Pro Gly Lys
        435                 440                 445

<210> SEQ ID NO 36
<211> LENGTH: 107
<212> TYPE: PRT
<213> ORGANISM: Artificial Sequence
<220> FEATURE:
<223> OTHER INFORMATION: Synthetic Construct

<400> SEQUENCE: 36

Asp Ile Leu Leu Thr Gln Ser Pro Ala Thr Leu Ser Val Thr Pro Gly
1               5                   10                  15

Asp Ser Val Ser Leu Ser Cys Arg Ala Ser Asp Ser Ile Ser Gly Ser
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Thr Asp Phe Thr Leu Ser Ile Asn Ser Val Glu Thr
65                  70                  75                  80

Glu Asp Phe Gly Met Tyr Phe Cys Gln Gln Ser Asn Ser Trp Pro Leu
                85                  90                  95

Asn Phe Gly Ala Gly Thr Lys Leu Glu Leu Lys
            100                 105

<210> SEQ ID NO 37
<211> LENGTH: 119
<212> TYPE: PRT
<213> ORGANISM: Artificial Sequence
<220> FEATURE:
<223> OTHER INFORMATION: Synthetic Construct
```

<400> SEQUENCE: 37

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Thr Met Ser Trp Val Arg Gln Thr Pro Glu Lys Arg Leu Glu Trp Val
        35                  40                  45

Ala Thr Ile Ser Gly Gly Gly Asn Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Leu Ser Ser Leu Arg Ser Glu Asp Thr Ala Leu Tyr Tyr Cys
                85                  90                  95

Ala Arg Pro Gly Tyr Asn Asn Tyr Tyr Phe Asp Tyr Trp Gly Gln Gly
            100                 105                 110

Thr Thr Leu Thr Val Ser Ser
        115

<210> SEQ ID NO 38
<211> LENGTH: 17
<212> TYPE: PRT
<213> ORGANISM: Artificial Sequence
<220> FEATURE:
<223> OTHER INFORMATION: Synthetic Construct

<400> SEQUENCE: 38

Thr Ile Ser Gly Gly Gly Gly Asn Thr Tyr Tyr Pro Asp Ser Val Lys
1               5                   10                  15

Gly

<210> SEQ ID NO 39
<211> LENGTH: 10
<212> TYPE: PRT
<213> ORGANISM: Artificial Sequence
<220> FEATURE:
<223> OTHER INFORMATION: Synthetic Construct

<400> SEQUENCE: 39

Pro Gly Tyr Asn Asn Tyr Tyr Phe Asp Tyr
1               5                   10

<210> SEQ ID NO 40
<211> LENGTH: 11
<212> TYPE: PRT
<213> ORGANISM: Artificial Sequence
<220> FEATURE:
<223> OTHER INFORMATION: Synthetic Construct

<400> SEQUENCE: 40

Arg Ala Ser Asp Ser Ile Ser Gly Ser Leu His
1               5                   10

<210> SEQ ID NO 41
<211> LENGTH: 7
<212> TYPE: PRT
<213> ORGANISM: Artificial Sequence
<220> FEATURE:
<223> OTHER INFORMATION: Synthetic Construct

<400> SEQUENCE: 41

Tyr Ala Ser Gln Ser Ile Ser
1               5

<210> SEQ ID NO 42
<211> LENGTH: 9
<212> TYPE: PRT
<213> ORGANISM: Artificial Sequence
<220> FEATURE:
<223> OTHER INFORMATION: Synthetic Construct

<400> SEQUENCE: 42

Gln Gln Ser Asn Ser Trp Pro Leu Asn
1               5

<210> SEQ ID NO 43
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (7)..(7)
<223> OTHER INFORMATION: Xaa at position 7 = Phe or Gly
<220> FEATURE:
<221> NAME/KEY: MISC_FEATURE
<222> LOCATION: (8)..(8)
<223> OTHER INFORMATION: Xaa at position 8 = Gly or Asn

<400> SEQUENCE: 43

Thr Ile Ser Gly Gly Gly Xaa Xaa Thr Tyr Tyr Pro Asp Ser Val Lys
1               5                   10                  15
Gly

<210> SEQ ID NO 44
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa at position 4 = His or Asn

<400> SEQUENCE: 44

Pro Gly Tyr Xaa Asn Tyr Tyr Phe Asp Ile
1               5                   10

<210> SEQ ID NO 45
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa at position 4 = His or Asn
<220> FEATURE:
<221> NAME/KEY: MISC_FEATURE
<222> LOCATION: (10)..(10)
<223> OTHER INFORMATION: Xaa at position 10 = Ile or Tyr

<400> SEQUENCE: 45

Pro Gly Tyr Xaa Asn Tyr Tyr Phe Asp Xaa
1               5                   10

<210> SEQ ID NO 46
<211> LENGTH: 11
<212> TYPE: PRT
<213> ORGANISM: Artificial Sequence

```
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa at position 1 = His or Arg
<220> FEATURE:
<221> NAME/KEY: MISC_FEATURE
<222> LOCATION: (8)..(8)
<223> OTHER INFORMATION: Xaa at position 8 = Asn or Gly

<400> SEQUENCE: 46

Xaa Ala Ser Asp Ser Ile Ser Xaa Ser Leu His
1               5                   10

<210> SEQ ID NO 47
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 = Gly or Ala
<220> FEATURE:
<221> NAME/KEY: MISC_FEATURE
<222> LOCATION: (6)..(6)
<223> OTHER INFORMATION: Xaa at position 6 = Ile or Glu

<400> SEQUENCE: 47

Tyr Xaa Arg Gln Ser Xaa Gln
1               5

<210> SEQ ID NO 48
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 = Gly or Ala
<220> FEATURE:
<221> NAME/KEY: MISC_FEATURE
<222> LOCATION: (3)..(3)
<223> OTHER INFORMATION: Xaa at position 3 = Arg or Ser
<220> FEATURE:
<221> NAME/KEY: MISC_FEATURE
<222> LOCATION: (6)..(6)
<223> OTHER INFORMATION: Xaa at position 6 = Ile or Glu
<220> FEATURE:
<221> NAME/KEY: MISC_FEATURE
<222> LOCATION: (7)..(7)
<223> OTHER INFORMATION: Xaa at position 7 = Gln or Ser

<400> SEQUENCE: 48

Tyr Xaa Xaa Gln Ser Xaa Xaa
1               5

<210> SEQ ID NO 49
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa at position 4 = Glu or Ala

<400> SEQUENCE: 49
```

Gln Gln Ser Xaa Ser Trp Pro Leu His
1               5

<210> SEQ ID NO 50
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa at position 4 = Glu, Ala or Asn
<220> FEATURE:
<221> NAME/KEY: MISC_FEATURE
<222> LOCATION: (9)..(9)
<223> OTHER INFORMATION: Xaa at position 9 = His or Asn

<400> SEQUENCE: 50

Gln Gln Ser Xaa Ser Trp Pro Leu Xaa
1               5

<210> SEQ ID NO 51
<211> LENGTH: 119
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (102)..(102)
<223> OTHER INFORMATION: Xaa at position 102 = His or Asn

<400> SEQUENCE: 51

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Thr Met Ser Trp Val Arg Gln Ala Pro Gly Lys Gly Leu Glu Trp Val
        35                  40                  45

Ala Thr Ile Ser Gly Gly Gly Phe Gly Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Pro Gly Tyr Xaa Asn Tyr Tyr Phe Asp Ile Trp Gly Gln Gly
            100                 105                 110

Thr Thr Val Thr Val Ser Ser
        115

<210> SEQ ID NO 52
<211> LENGTH: 107
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (51)..(51)
<223> OTHER INFORMATION: Xaa at position 51 = Gly or Ala
<220> FEATURE:
<221> NAME/KEY: MISC_FEATURE
<222> LOCATION: (55)..(55)
<223> OTHER INFORMATION: Xaa at position 55 = Ile or Glu
<220> FEATURE:
<221> NAME/KEY: MISC_FEATURE
<222> LOCATION: (92)..(92)

-continued

<223> OTHER INFORMATION: Xaa at position 92 = Glu or Ala

<400> SEQUENCE: 52

```
Glu Ile Val Leu Thr Gln Ser Pro Ala Thr Leu Ser Leu Ser Pro Gly
1               5                   10                  15

Glu Arg Ala Thr Leu Ser Cys His Ala Ser Asp Ser Ile Ser Asn Ser
            20                  25                  30

Leu His Trp Tyr Gln Gln Lys Pro Gly Gln Ala Pro Arg Leu Leu Ile
        35                  40                  45

Tyr Tyr Xaa Arg Gln Ser Xaa Gln Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Xaa Ser Trp Pro Leu
                85                  90                  95

His Phe Gly Gly Gly Thr Lys Val Glu Ile Lys
                100                 105
```